United States Patent [19]

Ohhashi

[11] Patent Number: 5,315,665

[45] Date of Patent: May 24, 1994

[54] X-RAY COMPUTERIZED TOMOGRAPHY APPARATUS FOR OBTAINING CONSECUTIVE TOMOGRAPHIC IMAGES IN EITHER A FORWARD OR BACKWARD DIRECTION WITHOUT PERFORMING INTERPOLATION FOR VIEWS OVER AN ENTIRE 360

[75] Inventor: Akinami Ohhashi, Saitama, Japan

[73] Assignee: Kabushiki Kaisha Toshiba, Kawasaki, Japan

[21] Appl. No.: 853,046

[22] Filed: Mar. 18, 1992

[30] Foreign Application Priority Data

Mar. 20, 1991 [JP] Japan .................................. 3-57063
Mar. 22, 1991 [JP] Japan .................................. 3-58769

[51] Int. Cl.$^5$ ............................................ G06F 15/42
[52] U.S. Cl. .................... 382/6; 364/413.18; 364/413.21; 378/901
[58] Field of Search .......... 382/6; 364/413.13, 413.14, 364/413.16, 413.18, 413.19, 413.21; 378/901

[56] References Cited

U.S. PATENT DOCUMENTS

| | | | |
|---|---|---|---|
| 4,293,912 | 10/1981 | Walters ................................. | 382/6 |
| 4,495,645 | 1/1985 | Ohhashi ................................ | 382/6 |
| 5,073,911 | 12/1991 | Ozaki et al. ..................... | 364/413.21 |
| 5,212,717 | 5/1993 | Hada .............................. | 364/413.14 |
| 5,216,601 | 6/1993 | Crawford ....................... | 364/413.16 |

Primary Examiner—Leo H. Boudreau
Assistant Examiner—Larry J. Prikockis
Attorney, Agent, or Firm—Finnegan, Henderson, Farabow, Garrett & Dunner

[57] ABSTRACT

In a helical scanning X-ray CT apparatus, views at an m-th slice position are obtained by interpolating 360° views in a range next to the slice position in a forward direction in which the slice position number increases and 360° views in a range next to the slice position in the backward direction, and m-th tomographic image is reconstructed based on the interpolated views at the m-th slice position. An m-th backward image (mBI) is reconstructed based on the 360° views in the range next to the m-th slice position in the backward direction without interpolation and an m-th forward image (mFI) is reconstructed based on the 360° views in the range next to the m-th slice position in the forward direction without interpolation. An $(m+1)$BI is obtained by BP [CONV $(a-b)$] on the mBI and $(m+1)$FI is obtained by BP [CONV $(c-a)$] on the mFI. Here, BP: back projection, CONV: convolution, a: a view at the m-th slice position, b: a view which is separated from "a" by 360°, and c: a view which is separated from "a" by 360°. An $(m+1)$th image is obtained as follows:

$$(m+1)I = mI + DW \times \{(m+1)FI - (m+1)BI\}$$

where DW is an inclination of the coefficients of the interpolation (primary interpolation).

15 Claims, 15 Drawing Sheets

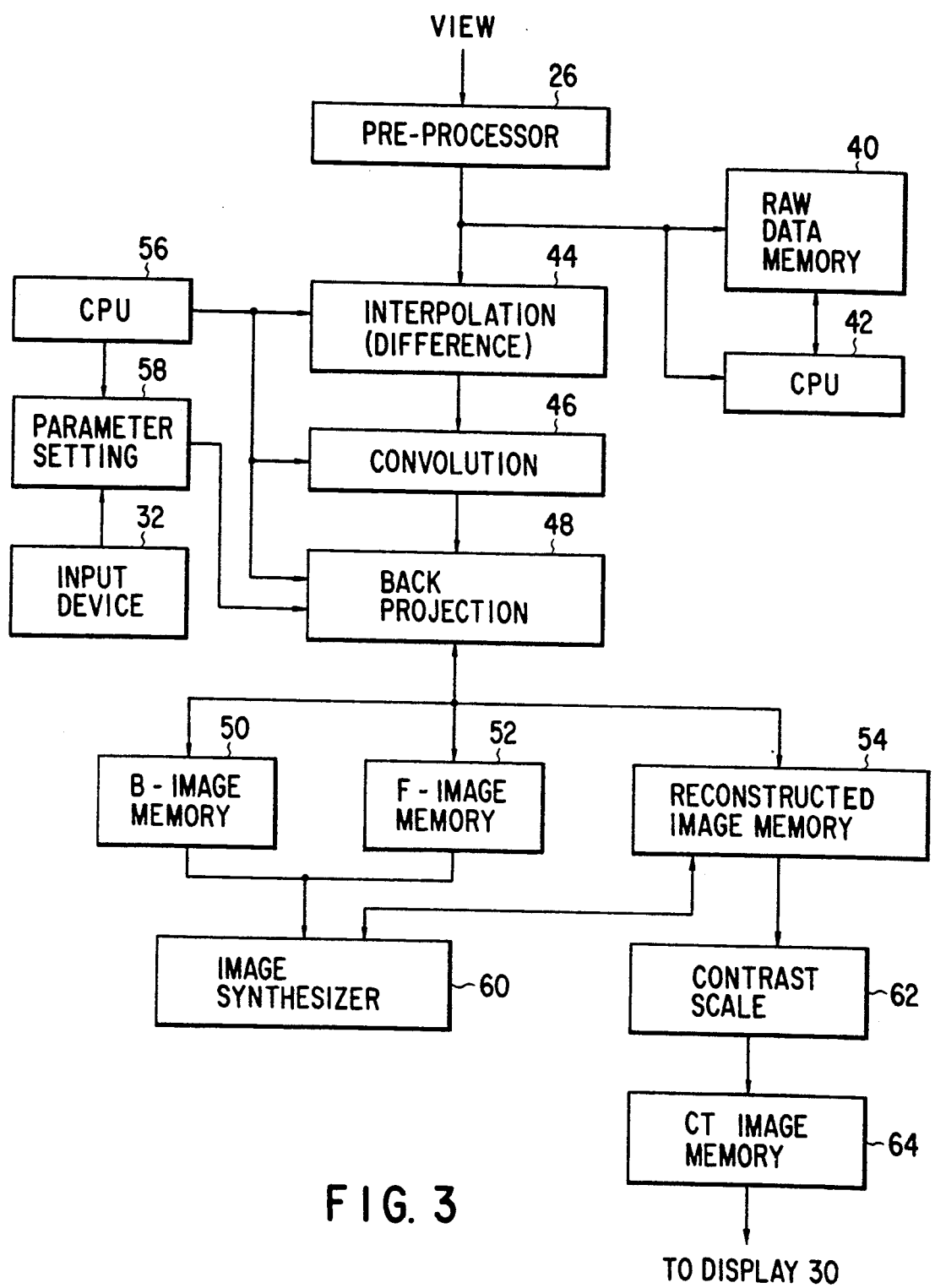
F I G. 3

X-RAY COMPUTERIZED TOMOGRAPHY APPARATUS FOR OBTAINING CONSECUTIVE TOMOGRAPHIC IMAGES IN EITHER A FORWARD OR BACKWARD DIRECTION WITHOUT PERFORMING INTERPOLATION FOR VIEWS OVER AN ENTIRE 360

BACKGROUND OF THE INVENTION

1. Field of the Invention

The present invention relates to an X-ray computerized tomography apparatus (hereinafter referred to as an X-ray CT apparatus) and, more particularly, to image reconstruction in, for example, a third generation X-ray CT apparatus using a helical scan scheme in which the projection is performed while the bed is moved.

2. Description of the Related Art

FIG. 1 is a schematic block diagram showing a processing circuit associated with image reconstruction processing in a conventional X-ray CT apparatus. Projection data or views (hereinafter referred to as views) from a data acquisition system (not shown) are supplied to a pre-processing circuit 2. The preprocessing circuit 2 performs a logarithmic conversion and various corrections on the views. A raw data memory 4 and a central processing unit (hereinafter referred to as a CPU) 6 are connected to the output terminal of the pre-processing circuit 2. An output from the preprocessing circuit 2 is stored, as a reconstructed image, in an image memory 12 through a convolution processing circuit (hereinafter referred to as a CONV circuit) 8 and a back projection processing circuit (hereinafter referred to as a BP circuit) 10. The reconstructed image data in the image memory 12 is supplied to contrast scale circuit 14 to be converted into a CT image data. The CT image data is stored in a CT image memory 14 and is supplied to a display device (not shown).

A CPU 16 is connected to the CONV circuit 8, the BP circuit 10 and the contrast scale circuit 14. In addition, a parameter setting device 18 for setting various parameters for back projection processing under the control of the CPU 16 is connected to the BP circuit 13. Although not shown, various buffers are included in the CONV circuit 8 and the BP circuit 10 to perform high-speed reconstruction processing.

In such a conventional apparatus, data associated with 360° or 180° views is basically processed as a group (unit). Image reconstruction is independently performed at each slice position by using a group of 360° or 180° views. For this reason, when images at a large number of slice positions are to be reconstructed, the time required for reconstruction is inevitably prolonged in proportion to the number of images. In addition, if reconstructed images are to be stored, the method of reconstructing images at a large number of slice positions one by one requires a large storage area.

Under the circumstances, methods of efficiently reconstructing images at many consecutive slice positions have been considered. For example, a reconstruction method is disclosed in U.S. Pat. No. 4,495,645.

This conventional continuous slice reconstruction method, however, is associated with a continuous scan scheme at the same slice position. No conventional methods have been proposed to allow efficient reconstruction of images at consecutive slice positions in the helical scan scheme.

SUMMARY OF THE INVENTION

Accordingly, it is an object of the present invention to efficiently reconstruct images at a large number of consecutive slice positions in an X-ray CT apparatus using the helical scan scheme.

It is another object of the present invention to provide an X-ray CT apparatus using the helical scan scheme, which allows continuous observation of the interior of a human body by continuously displaying images at many consecutive slice positions.

It is still another object of the present invention to provide an X-ray CT apparatus using the helical scan scheme, which can reduce the number of images to be stored by displaying images at many consecutive slice positions upon image reconstruction.

According to the present invention, there is provided an X-ray computerized tomography apparatus irradiating an X-ray onto an object to acquire views during a movement of a bed for supporting the object in a helical scanning scheme, comprising means for obtaining a tomographic image at a first slice position by performing a predetermined reconstruction processing with respect to a first group of views in a predetermined range which includes the first slice position, means for extracting a part of views from the first group of views which is not common to a second group of views which is necessary for reconstructing a tomographic image at a second slice position which is adjacent to the first slice position, and means for obtaining a tomographic image at the second slice position by performing the predetermined reconstruction processing with respect to the part views and synthesizing a result of reconstruction processing and the tomographic image at the first slice position.

According to the present invention, in the helical scan scheme, images at consecutive slice positions can be obtained at high speed. Therefore, by continuously changing the slice position in accordance with an operation of a command input device such as a mouse, the interior of a human body can be continuously observed, providing useful information for diagnosis.

Additional objects and advantages of the present invention will be set forth in the description which follows, and in part will be obvious from the description, or may be learned by practice of the present invention. The objects and advantages of the present invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the present invention and, together with the general description given above and the detailed description of the preferred embodiments given below, serve to explain the principles of the present invention in which:

FIG. 3 is a block diagram showing a reconstruction processing circuit of the first embodiment;

DETAILED DESCRIPTION OF THE PREFERRED EMBODIMENT

Figure 1:
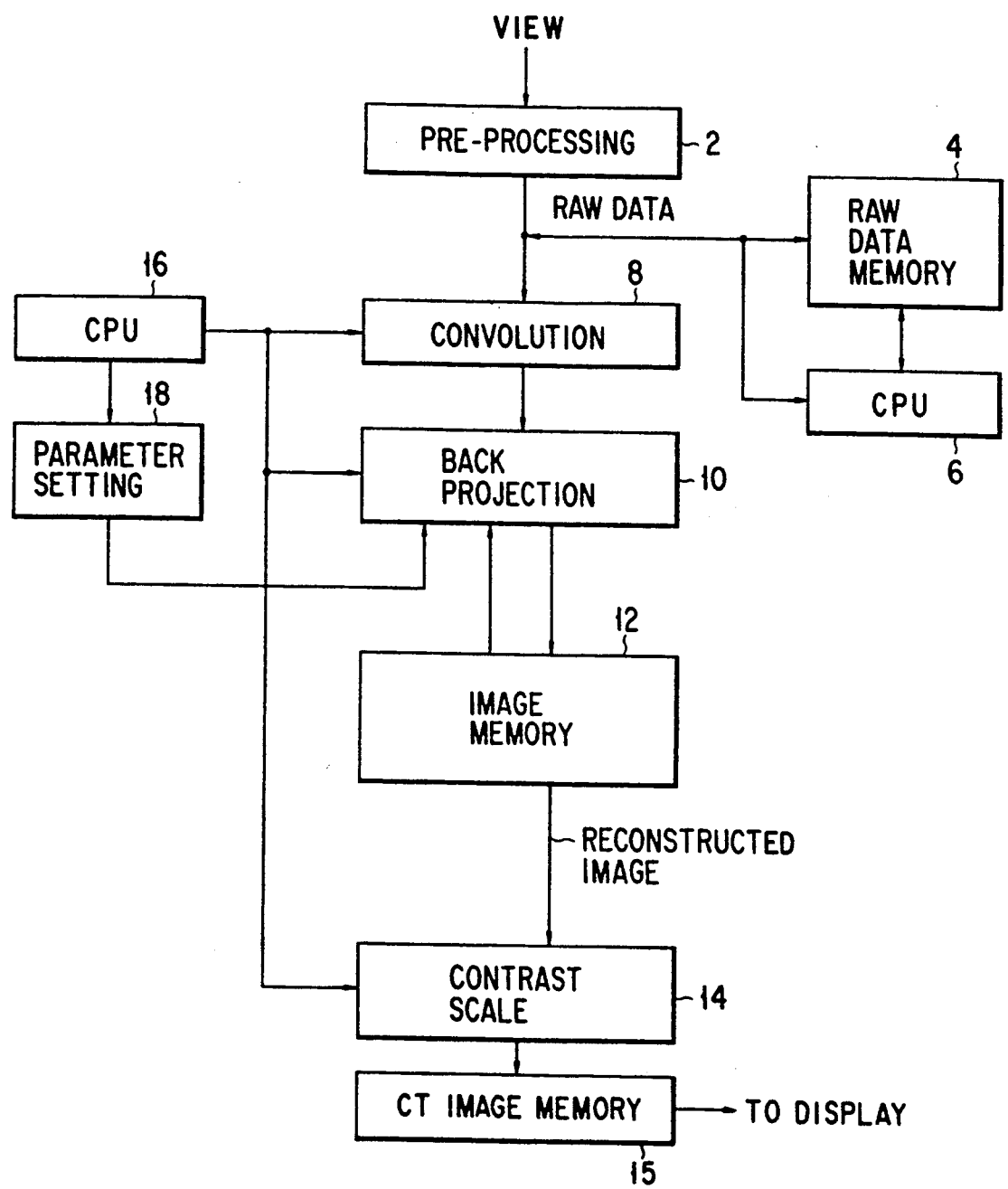
FIG. 1 is a block diagram showing a reconstruction processing circuit of a conventional X-ray CT apparatus.

A preferred embodiment of an X-ray CT apparatus according to the present invention will now be described with reference to the accompanying drawings. The principle of image reconstruction in the present invention will be described first. Note that all views in the present invention are acquired by the helical scan scheme. Assume that an image at a certain slice position will be referred to as the m-th image (an image of an image number m). This m-th image can be obtained by reconstructing views within a corresponding slice position range, which are obtained by performing primary interpolation of views within a range of view angles 720° including the slice position as the center. This reconstruction may be performed in the same manner as in the conventional helical scan scheme reconstruction processing.

An image at a slice position adjacent to the above-mentioned slice position is obtained by the following processing unique to the present invention, which is different from the above-described normal processing. 360° views acquired within a range which is next to the slice position of the m-th image in a backward direction in which the slice position number decreases are reconstructed into an image without performing interpolation. This image will be referred to as the m-th B-image. Similarly, 360° view acquired within a range which is next to the slice position of the m-th image in a forward direction in which the slice position number increases are reconstructed into an image without performing interpolation. This image will be referred to as the m-th F-image. In addition, assume that the distance a bed moves while an X-ray tube and an X-ray detector are rotated through one view angle to obtain 360° view is represented by d, and an image at a slice position which is separated from the slice position of the m-th image by the distance "d" in the forward direction is referred to as the (m+1)th image. In this case, assume that the moving direction of the bed is defined as a forward direction. For the sake of descriptive convenience, assume that the slice position coincides with the view position.

In order to obtain the (m+1)th image, the following images are obtained:

$$(m + 1)th\ B - image = m - th\ B - image + BP[CONV(a - b)] \quad (1)$$

$$(m + 1)th\ F - image = m - th\ F - image + BP[CONV(c - a)] \quad (2)$$

where
BP: back projection processing
CONV: convolution processing
a: a view at an m-th slice position
b: a view at a position which is separated from the m-th slice position by 360° in the backward direction
c: a view at a position which is separated from the m-th slice position by 360° in the forward direction The (m+1)th image is obtained from the above images as follows:

$$(m + 1)th\ image = m - th\ image + DW \times \quad (3)$$
$$((m + 1)th\ F\text{-image} - (m + 1)th\ B - image)$$

where DW: inclination of primary interpolation

Similarly, the (m-1)th image is obtained as follows:

$$(m - 1)th\ image = m - th\ image - DW \times \quad (3a)$$
$$(m - th\ F - image - m - th\ B - image)$$

According to the above principle, a CT image at each slice position can be simply obtained by a small number of calculation steps, and interpolation and reconstruction of 360° views at each slice position need not be performed. This makes it possible to obtain images at consecutive slice positions in a helical scan at high speed. If, therefore, the slice position of the m-th image is continuously changed by using a pointing device, such as a mouse or the like, images at the respective slice positions can be continuously displayed to allow continuous observation of the interior of a human body.

Figure 2:
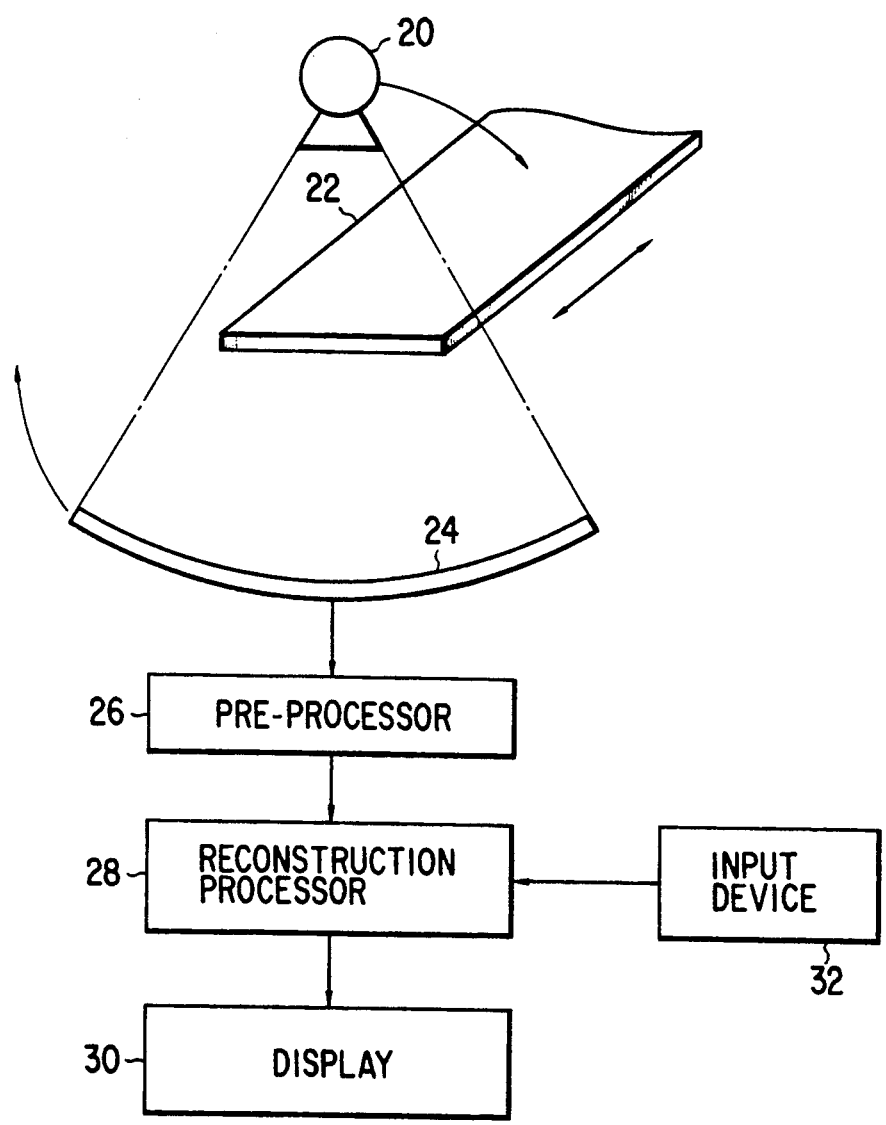
FIG. 2 shows the basic arrangement of an X-ray CT apparatus according to a first embodiment of the present invention.

The first embodiment of the present invention base on this principle will be described below. FIG. 2 is a block diagram showing a schematic arrangement of the X-ray CT apparatus of the first embodiment. In this case, a third generation X-ray CT apparatus will be exemplified. However, the present invention can be applied to apparatuses of other generations. In third generation CT apparatuses, a scanning is performed while an X-ray tube 20 and an X-ray detector 24 are rotated about a bed 22. In many third generation CT apparatuses, the rotational direction of these components is reversed clockwise and counterclockwise for every scan. Recently, however, some third generation CT apparatuses have employed a scheme for scanning by continuously rotating the components in the same direction. In general, while the X-ray tube 20 and the X-ray detector 24 are rotated through 360° to perform a scanning operation, the bed 22 is kept stopped. The present invention, however, employs a scanning scheme called helical scanning, in which the bed 22 is also continuously moved in synchronization with the X-ray tube 22 and the X-ray detector 24 to helically scan an object to be examined. According to this scheme, tomographic images of many slices can be imaged at high speed.

The output of the X-ray detector 24 is supplied to a reconstruction processor 28 through a pre-processor 26. The pre-processor 26 performs a logarithmic conversion and various corrections on the detected signal from the detector 24. An input device 32, such as a keyswitch or a mouse, is connected to the reconstruction processor 28. The output of the reconstruction processor 28 is supplied to a display 30 to be displayed.

FIG. 3 is a block diagram showing a schematic arrangement of the reconstruction processor 28 in FIG. 2. A raw data memory 40 and a CPU 42 are connected to the output terminal of the pre-processor 26. An output from the pre-processor 26 is supplied to a convolution processing (CONV) circuit 46 through an interpolation (difference) processing circuit 44. The interpolation processing circuit 44 serves as a difference processing circuit upon setting interpolation constants to be $-1$ and $+1$. An output from the CONV circuit 46 is supplied to a B-image memory 50, an F-image memory 52 and a reconstructed image memory 54 through a back projection processing (BP) circuit 48. Note that the definitions of the B-image and F-image have already been discussed. A CPU 56 is also connected to the interpolation processing circuit 44, the CONV circuit 46 and the BP circuit 48. In addition, a parameter setting device 58 is connected to the BP circuit 48. Outputs from the B-image memory 50, the F-image memory 52 and the reconstructed image memory 54 are synthesized by an image synthesizing circuit 60. The resulting data is supplied to the reconstructed image memory 54 again. An output from the reconstructed image memory 54 is supplied to a CT image memory 64 through a contrast scale circuit 62. An output from the CT image memory 64 is displayed by the display device 30 (FIG. 2). An input device 32 is connected to the parameter setting circuit 58.

Table 1 shows a set of views picked up (acquired) by helical scanning.

TABLE 1

| View number | View angle (°) | Bed position | Image number |
|---|---|---|---|
| 1 | 1 | 1d | |
| 2 | 2 | 2d | |
| . | . | . | |
| . | . | . | |
| . | . | . | |
| n | n | nd | |
| . | . | . | |
| . | . | . | |
| . | . | . | |
| 360 | 360 | 360d | 1 |
| 361 | 1 | 361d | 2 |
| 362 | 2 | 362d | 3 |
| . | . | . | . |
| . | . | . | . |
| . | . | . | m |
| . | . | . | m + 1 |
| . | . | . | . |
| 720 | 360 | 720d | 361 |
| 721 | 1 | 721d | 362 |

TABLE 1-continued

| View number | View angle (°) | Bed position | Image number |
|---|---|---|---|
| 722 | 2 | 722d | 363 |
| . | . | . | . |
| . | . | . | . |
| 7200 | 360 | 7200d | 6841 |

Figure 4:
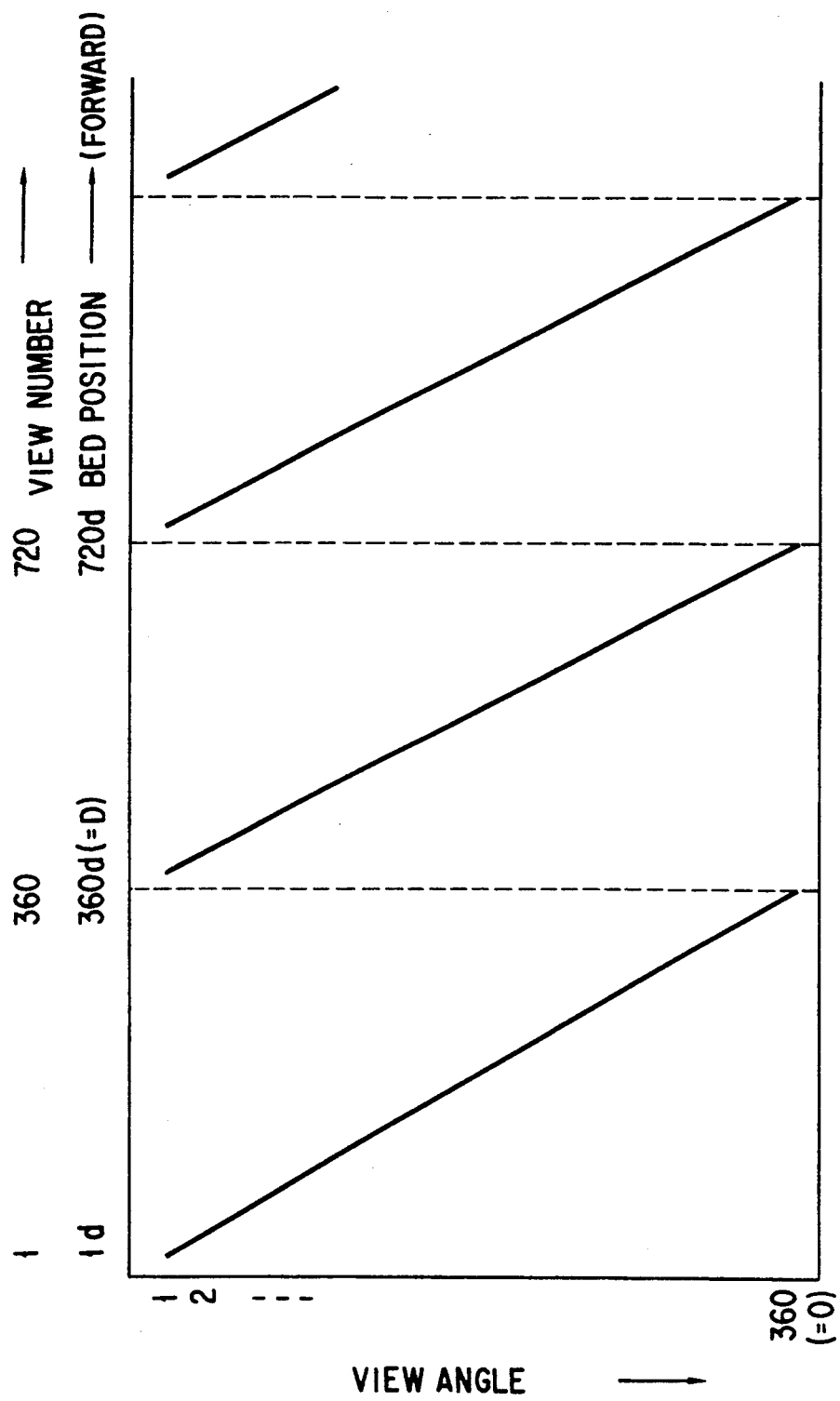
FIG. 4 is a view showing a state of helical scanning in present invention.

FIG. 4 shows the views schematically.

In Table 1 and FIG. 4, reference symbol d denotes the distance the bed moves while the X-ray tube and the X-ray detector are rotated by one view angle. Strictly speaking, the bed positions and the view angles are continuous. However, Table 1 and FIG. 4 shows values obtained at the middle of each data acquisition time as representative values.

Table 1 shows a case wherein projection is performed per rotation of the X-ray tube and the X-ray detector by 1°. Therefore, 360 views are obtained per one rotation. During one rotation, the bed is moved by $D = 360d$. For example, such projections are consecutively performed 20 times. In this case, the length of scanning is 20D, and the number of the obtained views is 7,200.

Although tomographic images of a large number of slices can be scanned at high speed by helical scanning, mathematically precise tomographic images cannot be obtained for the following reason. In order to reconstruct a tomographic image from the view images, view images of 180° or more are required for a single slice. In helical scanning, since a slice subjected to projection is continuously moved, view images of 180° or more for a single slice cannot be obtained. However, since the view image has a predetermined slice thickness, a practically satisfactory tomographic image can be obtained unless the bed is moved too fast.

In order to reconstruct a tomographic image in the helical scan scheme, a pseudo view image lacking at a reconstruction position must be calculated from view images at other slice positions. There are two typical types of methods of calculating pseudo views. In the first method, two views of the same view angle, projected at a position nearest to a slice position, are interpolated. In the second method, reflection data are formed by a so-called reflection method and are interpolated in the same manner. The present invention provides a scheme for efficiently executing the first method in reconstruction of continuous images.

A reconstruction method according to the first embodiment will be described below with reference to Table 1 and FIG. 4. Reconstruction of the second image having image number 2 will be described as an example. The slice position of the second image corresponds to "361d" in the bed position. Since 361st view is data obtained by projection at this position, although view of view angle of 1° exists, views of other angles do not exist. Each lacking view is obtained by interpolating two views of the same angle, obtained at near slice positions. For example, interpolated view of angle 2° can be obtained from a second view and 362nd view by interpolation. In many cases, interpolation is performed by primary interpolation of the distance between the position of view and the slice position of an image. Therefore, the interpolated view of angle 2° with respect to the second image is obtained as follows:

$$2PP2 = P2 \times WB2 + P362 \times WF2 \qquad (4)$$

where 2PP2: interpolated view of angle 2° with respect to the second image
P2: the second view
P362: 362nd view
WB2, WF2: interpolation coefficients The interpolation coefficients WB2 and WHF2 are represented as follows:

$$WB2 = d/360d = 1/360 \quad (5)$$

$$WF2 = (360d - d)/360d = 359/360 \quad (6)$$

Hereinafter, it is defined that "m" is an image number and "n" is an interpolated view number (1 to 360). Note that view of the same view angle as that of view at the slice position of the image is represented by n =1, i.e., first interpolated view. For example, interpolated view of angle 1° and interpolated view of angle 2° are respectively obtained as the first interpolated view with respect to the second and third images. The value n is increased in the direction in which the view number is increased with reference to it. Therefore, interpolated view of angle 2° and interpolated view of angle 3° correspond to n=2, i.e., the second interpolated view, for the second and third images, respectively.

If mPPn: n-th interpolated view for m-th image
Pj: j-th view (P0=0)
Pk: k-th view (Pk=0 if k>the number of all the views)

$$j = m + 358 + n - 360 \quad (7)$$

$$k = j + 360 \quad (8)$$

then, $$mPPn = Pj \times WBn + Pk \times WFn \quad (9) \ (n=1 \text{ to } 360)$$

where WBn and WFn are interpolation coefficients for the n-th interpolated view. These coefficients are represented as follows:

$$WBn = (n-1)/360 \quad (10)$$

$$WFn = (361-n)/360 \quad (11)$$

If CONV: convolution
BP: back projection
mI: m-th image
mQQ: set of mPPn (n=1 to 360)
then, the m-th image mI is obtained as follows:

$$mI = BP[CONV(mQQ)] \quad (12)$$

In order to describe reconstruction of continuous slice images according to the present invention, images termed a B-image and an F-image are defined by the following equations:

$$mBI = BP[CONV(mBPJ)] \quad (13)$$

$$mFI = BP[CONV(mFPK)] \quad (14)$$

where
mBI: B-image (backward image) with respect to m-th image
mFI: F-image (forward image) with respect to m-th image
mBPj: set of Pj (j=m−1 to m+358)
mFP: set of Pk (k=j+360)

A method of obtaining an (m+1)th B-image "(m+1)BI" and an (m+1)th F-image "(m+1)FI" from the m-th B-image mBI and the m-th F-image mFI will be described next.

The images mBI and mFI, and (m+1)BI and (m+1)FI are images reconstructed from views of view angles of 360°, and differ from each other by one view. Therefore, the images (m+1)BI and (m+1)FI can be obtained in the following manner by the scheme disclosed in the U.S. Pat. No. 4,495,645 described above.

$$(m+1)BI = mBI + BP[CONV(SBPm+1)] \quad (15)$$

$$(m+1)FI = mFI + BP[CONV(SFPm+1)] \quad (16)$$

where $$SBPm+1 = P(m+359) - P(m-1) \quad (17)$$

$$SFPm+1 = P(m+719) - P(m+359) \quad (18)$$

Similarly, images (m−1)BI and (m−1)FI can be obtained from the images mBI and mFI as follows:

$$(m-1)BI = mBI + BP[CONV(SMBPm-1)] \quad (19)$$

$$(m-1)FI = mFI + BP[CONV(SMFPm-1)] \quad (20)$$

where $$SMBPm-1 = P(m-2) - P(m+358) \quad (21)$$

$$MFPm-1 = P(m+358) - P(m+718) \quad (22)$$

A procedure for image reconstruction in this embodiment will be described in detail below with reference to the flow chart shown in FIG. 5. The flow chart is controlled by the CPUs 42 and 56.

In step #10, views are acquired by helical scanning.
In step #12, an image number (slice position number) "m" of an image displayed as a current image is arbitrarily determined and input through the input device 32.

In step #14, the current image (m-th image) is reconstructed according to equation (12) and displayed. In step #16, the current B-image (mB-image) is reconstructed according to equation (13). In step #18, the current F-image (mF image) is reconstructed according to equation (14). Parameters for the reconstructed image, the B-image and the F-image and the convolution function are supplied to the interpolation circuit 44 CONV circuit 46 and BP circuit 48 from the CPU 56.

In step #20, it is determined whether or not a direction designating switch included in the input device 32 is operated. Stated another way, it is determined whether or not another image adjacent to the current m-th image is to be reconstructed continuously. If it is determined that the direction designating switch is not operated, the flow waits for the operation of the direction designating switch at step #20. If it is determined that the direction designating switch is 7° operated, it is determined in step #22 whether an adjacent image in the direction in which the image number increases (forward direction) or decreases (backward direction) is to be reconstructed continuously. In the case of the image reconstruction in the forward direction, the flow advances to step #24. In the case of the image reconstruction in the backward direction, the flow advances to step #34.

In step #24, the (m+1)th B-image is reconstructed according to equation (15). Similarly, in step #26, the (m+1)th F-image is reconstructed according to equation (16). In step #28, the (m+1)th image at a slice position (m+1) is reconstructed by synthesizing the mI, (m+1)FI and (m+1)BI as follows:

$$(m+1)I = mI + DW[(m+1)FI - (m+1)BI] \quad (23)$$

where DW is an inclination of coefficients for primary interpolation and is represented as follows:

$$\begin{aligned} DW &= WB(n+1) - WBn \\ &= -[WF(n+1) - WFn] \\ &= 1/360 \end{aligned} \quad (24)$$

In step #30, m=m+1 is set. In step #32, the CT image corresponding to the image (m+1)I obtained in step #28 is displayed and the flow returns to step #20. In this manner, by sequentially incrementing the value "m", images at slice positions sequentially shifted in the forward direction can be continuously observed.

In step #34, the (m−1)th image at a slice position (m−1) is obtained by synthesizing the mI, mFI and mBI as follows:

$$(m-1)I = mI - DW \times [mFI - mBI] \quad (25)$$

In step #36, the (m−1)th B-image is reconstructed according to equation (19). Similarly, in step #38, the (m−1)th F-image is reconstructed according to equation (20). In step #40, m=m−1 is set. In step #42, the CT image corresponding to the image (m−1)I obtained in step #34 is displayed and the flow returns to step #20. In this manner, by sequentially decrementing the value "m", images at slice positions sequentially shifted in the backward direction can be continuously observed.

Equation (25) will be proved next. Equation (25) is rewritten as follows:

$$mI = (m-1)I + DW[mFI - mBI] \quad (26)$$

If m=m−1 is set in equation (12): mI=BP[CONV(mQQ)], the following equation can be obtained:

$$(m-1)I = BP[CONV((m-1)QQ)] \quad (27)$$

From equations (12) and (27), the following equation can be obtained:

$$mI - (m-1)I = BP[CONV((m-1), mRR)] \quad (28)$$

where ((m−1), mRR) is a difference set obtained from a set mQQ and a set (m−1)QQ. The set mQQ is a set of mPPn (n=1 to 360) and hence can be expressed as follows:

$$mPP1 = P(m-1) \times WB1 + P(m+359) \times WF1$$
$$mPP2 = Pm \times WB2 + P(m+360) \times WF2$$
$$\vdots$$
$$mPP360 = P(m+358) \times WB360 + P(m+718) \times WF360$$

Similarly, the set (m − 1)QQ can be expressed as follows:
$$(m-1)PP1 = P(m-2) \times WB1 + P(m+358) \times WF1$$
$$(m-1)PP2 = P(m-1) \times WB2 + P(m+359) \times WF2$$
$$\vdots$$
$$(m-1)PP360 = P(m+357) \times WB360 + P(m+717) \times WF360$$

Therefore, the difference set ((m − 1), mRR) can be expressed as follows:
$$-P(m-2) \times WB1 - P(m+358) \times WF1$$
$$P(m-1) \times (WB1 - WB2) + P(m+359) \times (WF1 - WF2)$$
$$\vdots$$
$$P(m+357) \times (WB359 - WB360) + P(m+717) \times (WF359 - WF360)$$
$$P(m+358) \times WB360 + P(m+718) \times WF360$$

From equation (24),
$$WB(n) - WB(n+1)$$
$$= WF(n) - WF(n+1)$$
$$= -DW$$

Therefore, if this value is substituted into the above set to group views of the same view angle, the difference set ((m−1), mRR) is represented as follows:

$$-P(m-2) \times WB1 - DW \times P(m-1) + DW \times P(m+359)$$
$$\vdots$$
$$-DW \times P(m+357) + DW \times P(m+717) - P(m+358) \times (WF1 - WB360) + P(m+718) \times WF360$$

In this case, (WF1−WB360)=1/360=DW, WB1=0 and WF360=1/360=DW. If these values are substituted into the above set to rearrange it, the set ((m−1), mRR) can be represented as follows:

$$\begin{aligned} &-DW \times (P(m-1), \ldots P(m+358)) + DW \times \\ &\quad (P(m+359), \ldots P(m+718)) \\ &= -DW \times mBPj + DW + mFPk \end{aligned} \quad (29)$$

If this equation (29) is substituted into equation (28), the following equation can be obtained:

$$\begin{aligned} mI - (m-1)I &= BP[CONV((m-1), mRR)] \quad (30)\\ &= BP[CONV(-DW \times mBPj + DW \times mFPk)] \\ &= DW \times BP[CONV(mFPk)] - DW \times \\ &\quad BP[CONV(mBPj)] \\ &= DW \times (mFI - mBI) \end{aligned}$$

Equation (30) can be rewritten as mI=(m−1)I+DW×(mFI−mBI), and hence equation (26) can be obtained. Similarly, equation (23) can be obtained by setting m=m+1 in equation (26).

The details of steps in FIG. 5 will be described.

Figure 5:
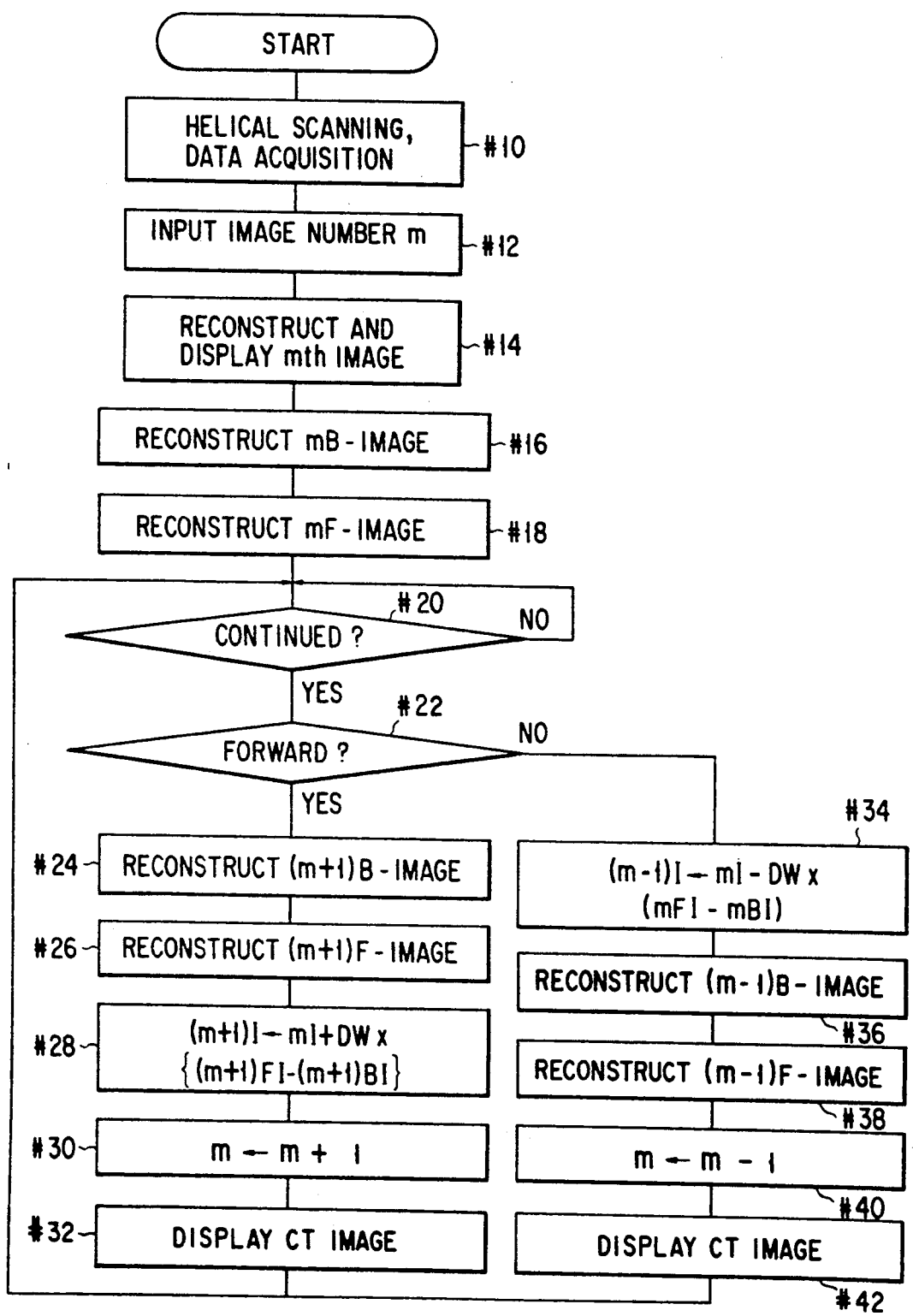
FIG. 5 is a flow chart showing the process of reconstructing continuous images in the first embodiment.
Figure 6:
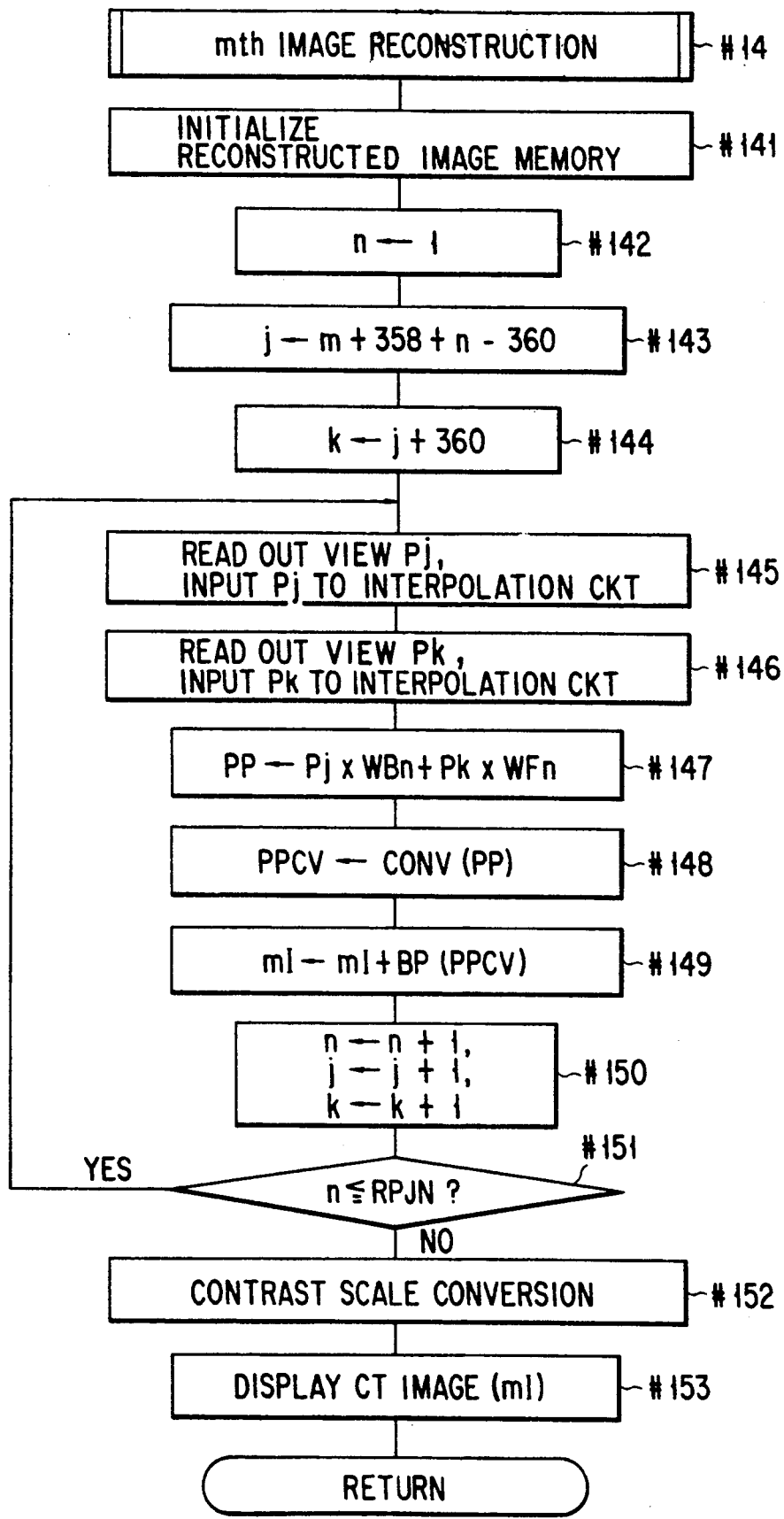
FIG. 6 is a detailed flow chart showing reconstruction processing of the m-th image in the flow chart in FIG. 5.

FIG. 6 is a detailed flow chart of step #14 of FIG. 5 for reconstructing the m-th image. Assume that the number of interpolated views necessary for obtaining the reconstructed image is RPJN. In step #141, the CPU 56 sends forth such instructions to the interpolation circuit 44, CONV circuit 46 and BP circuit 48 that indicates the reconstruction of the first image and initializes the reconstructed image memory 54. The reconstructed image data is reset to zero.

In step #142, n =1 is set. In step #143, j=m+358+n−360 is set. In step #144, k=j+360 is set. In step #145, the CPU 42 reads out j-th view Pj (P₀=0) from the raw data memory 40 and transfers it to the interpolation circuit 44. In step #146, the CPU 42 reads out k-th view Pk (Pk=0, if k>total number of views) and transfers it to the interpolation circuit 44.

In step #147, n-th interpolated view PP for the m-th image is obtained as follows:

$$PP = Pj \times WBn + Pk \times WFn \quad (31)$$

where WBn and WFn are interpolation coefficients for the n-th interpolated view.

In step #148, the CONV circuit 46 performs convolution processing of the output PP from the interpolation circuit 44 with the convolution function. In step #149, the BP circuit 48 performs back projection (addition) of a convolution result PPCV by superposing it on the image stored in the reconstructed image memory 54. The result of back projection is stored in the reconstructed image memory 54.

In step #150, n=n+1, j=j+1 and k=k+1 are set. In step #151, it is determined whether n is not larger than RPJN. If YES in step #151, the flow returns to step #145. If NO in step #151, the flow advances to step #152. In this case, the reconstructed image is stored in the reconstructed image memory 54.

In step #152, contrast scale conversion of all the pixels of the reconstructed image is performed in units of pixels by the contrast scale circuit 62 to form a CT image. The CT image is then stored in the CT image memory 64. Contrast scale conversion is a known technique and is generally performed according to the following equation:

$$PV = a \times RPV + b \quad (32)$$

where
PV: pixel value of CT image
RPV: pixel value of reconstructed image
a, b: constants The constants a and b are generally determined in accordance with the apparatus and X-ray tube voltages such that the CT values of water and air are respectively set to be 0 and −1,000.

In step #153 the current CT image (mI) is transferred to the display 30 to be displayed.

Figure 7:
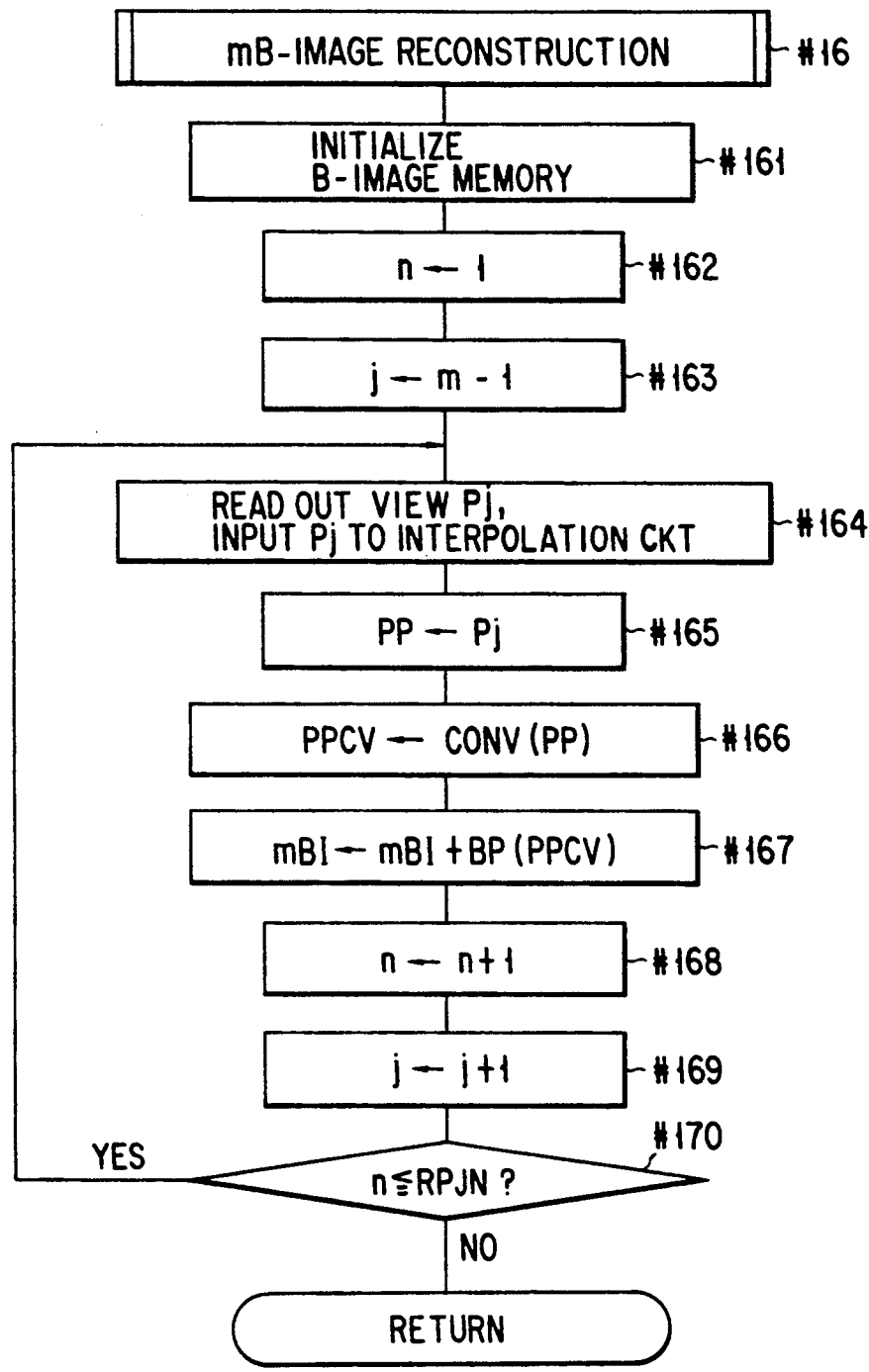
FIG. 7 is a detailed flow chart showing reconstruction processing of the m-th B-image in the flow chart in FIG. 5.

FIG. 7 is a detailed flow chart of step #16 of FIG. 5 for reconstructing the mB-image. In step #161, the CPU 56 sends forth such instructions to the interpolation circuit 44, CONV circuit 46 and BP circuit 48 that indicate the reconstruction of the first B-image and initialize the B-image memory 50. The B-image data is reset to zero.

In step #162, n=1 is set. In step #163, j=m−1 is set. In step #164, the CPU 42 reads out j-th view Pj from the raw data memory 40 and transfers it to the interpolation circuit 44.

In this case, since interpolation coefficients of 1 and 0 are set in the interpolation circuit 44, the interpolation circuit 44 simply passes the input data and stores it as the output PP without performing any operation in step #165. L In step #166, the CONV circuit 46 performs convolution processing of the output PP from the interpolation circuit 44 with the convolution function. In step #167, the BP circuit 48 performs back projection (addition) of a convolution result PPCV by superposing it on the image stored in the B-image memory 50. The result of back projection is stored in the B-image memory 50.

In step #168, n=n+1 is set. In step #169, j=j+1 is set. In step #170, it is determined whether n is not larger than RPJN. If YES in step #170, the flow returns to step #164. If NO in step #170, the flow ends. In this case, the current B-image mBI is reconstructed and stored in the B-image memory 50.

Figure 8:
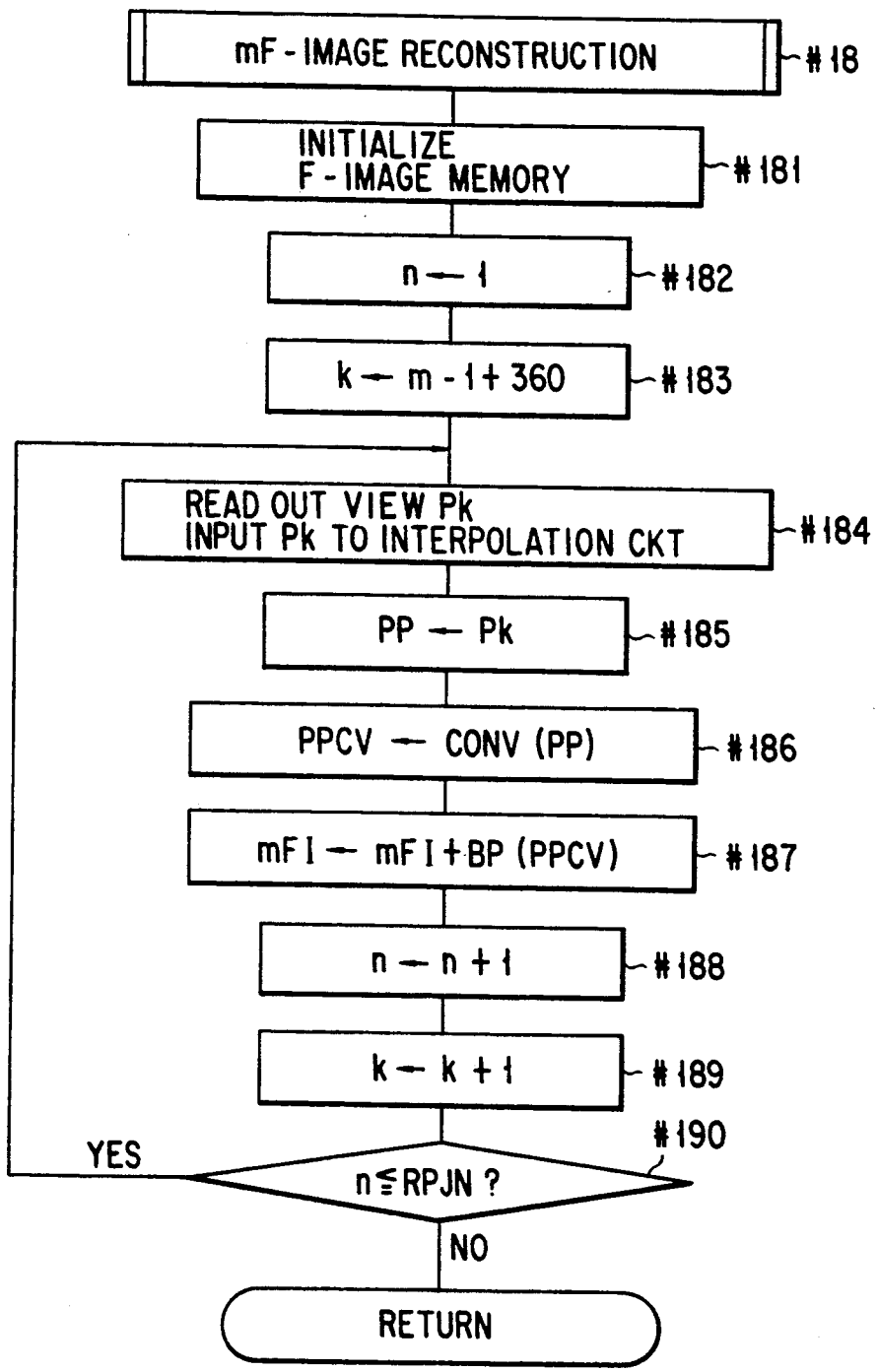
FIG. 8 is a detailed flow chart showing reconstruction processing of the m-th F-image in the flow chart in FIG. 5.

FIG. 8 is a detailed flow chart of step #18 of FIG. 5 for reconstructing the mF-image. In step #181, the CPU 56 sends forth such instructions to the interpolation circuit 44, CONV circuit 46 and BP circuit 48 that indicate the reconstruction of the first F-image and initialize the F-image memory 52. The F-image data is reset to zero.

In step #182, n=1 is set. In step #183, k=m−1+360 is set. In step #184, the CPU 42 reads out k-th view Pk from the raw data memory 40 and transfers it to the interpolation circuit 44.

In this case, since interpolation coefficients of 1 and 0 are set in the interpolation circuit 44, the interpolation circuit 44 simply passes the input data and stores it as the output PP without performing any operation in step #185.

In step #186, the CONV circuit 46 performs convolution processing of the output PP from the interpolation circuit 44 with the convolution function. In step #187, the BP circuit 48 performs back projection (addition) of a convolution result PPCV by superposing it on the image stored in the F-image memory 52. The result of back projection is stored in the F-image memory 52.

In step #188, n=n+1 is set. In step #189, k=k+1 is set. In step #190, it is determined whether n is not larger than RPJN. If YES in step #190, the flow returns to step #184. If NO in step #190, the flow ends. In this case, the current F-image mFI is reconstructed and stored in the F-image memory 52.

Figure 9:
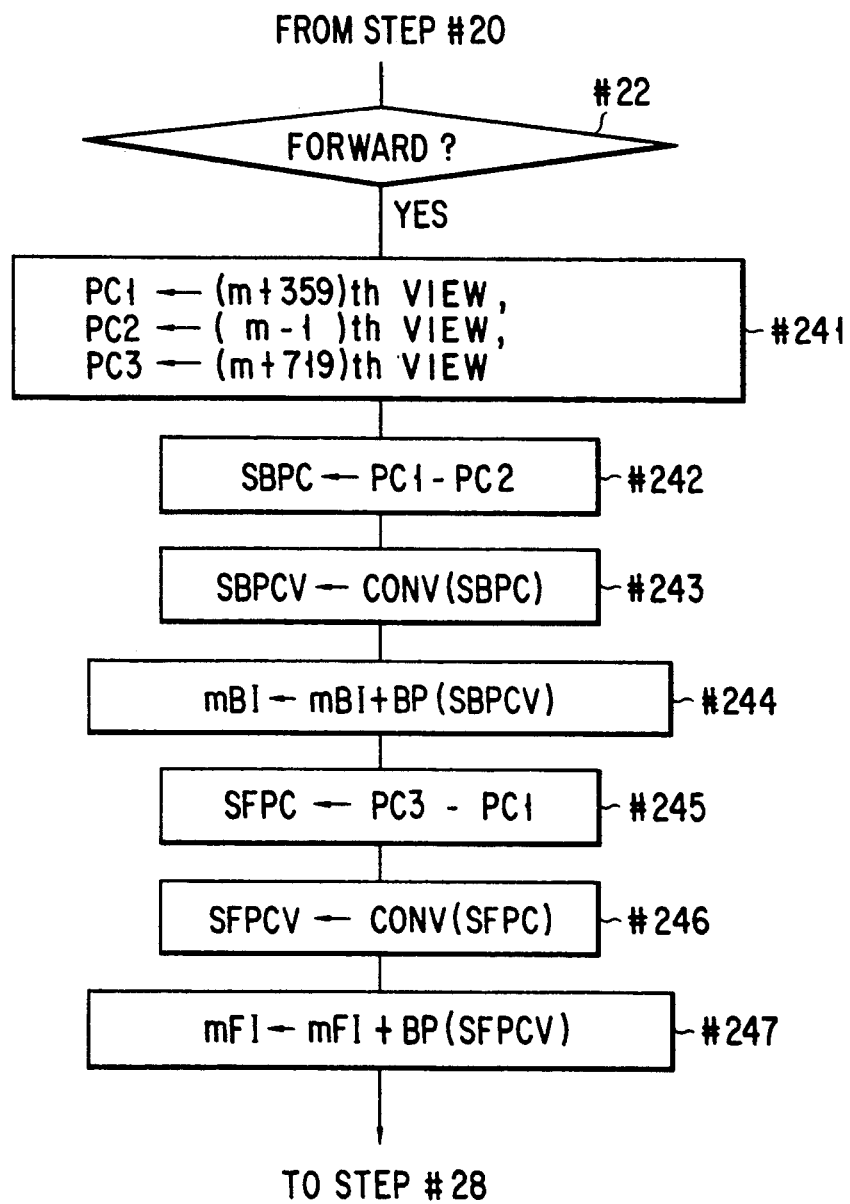
FIG. 9 is a detailed flow chart showing reconstruction processing of the (m +1)th B-image and the (m+1)th F-image in the flow chart in FIG. 5.

FIG. 9 is a detailed flow chart of steps #24 and #26 of FIG. 5 for reconstructing the (m+1)B-image and (m+1)F-image. Assumed that the mI, mBI and mFI are stored in the reconstructed image memory 54, B-image memory 50 and F-image memory 52, respectively.

First, the CPU 56 sends forth such instructions to the interpolation circuit 44, CONV circuit 46 and BP circuit 48 that indicate the reconstruction of the forward image, the inclination DW of the primary interpolation, the parameters necessary for the back projection (for the B-image and F-image), the convolution function and the like. Note that data which has already been stored in the reconstruction processing unit need not be transferred.

In step #241, the CPU 42 reads out three views, i.e., the (m+359)th view, the (m−1)th view and the (m+719)th view, from the raw data memory 40, and supplies them to the interpolation (difference) circuit 44. In this case, these views are respectively represented by PC1, PC2 and PC3.

In step #242, the interpolation (difference) circuit 44 performs a calculation of PC1−PC2, and transfers the calculation result, as a difference SBPC, to the CONV circuit 46. In step #243, the CONV circuit 46 performs convolution processing of the difference SBPC with the convolution function. Convolution processing can be performed by using a known technique. The convolution result is represented by SBPCV. In step #244, the BP circuit 48 performs back projection of the convolution result SPBCV by superposing (adding) the convolution result SBPCV on the B-image mBI in the B-image memory 50. Back projection processing can be performed by using a known technique. The parameters necessary for the back projection processing of the B-image are generated from the parameter setting device 58 under the control of the CPU 56 and are transferred to the BP circuit 48.

In step #245, the interpolation (difference) circuit 44 performs a calculation of PC3−PC1, and transfers the calculation result, as a difference SFPC, to the CONV circuit 46. In step #246, the CONV circuit 46 performs convolution processing of the difference SFPC with the convolution function. The convolution result is represented by SFPCV. In step #247, the BP circuit 48 performs back projection of the convolution result SPFCV by superposing (adding) the convolution result SFPCV on the F-image mFI in the F-image memory 52. The parameters necessary for the back projection processing of the F-image are generated from the parameter setting device 58 under the control of the CPU 56 and are transferred to the BP circuit 48. Note that step #242 to step #244 and step #245 to step #247 may be partly or completely multiplexed to be executed by different circuits, different printed circuit boards, or different units.

Figure 10:
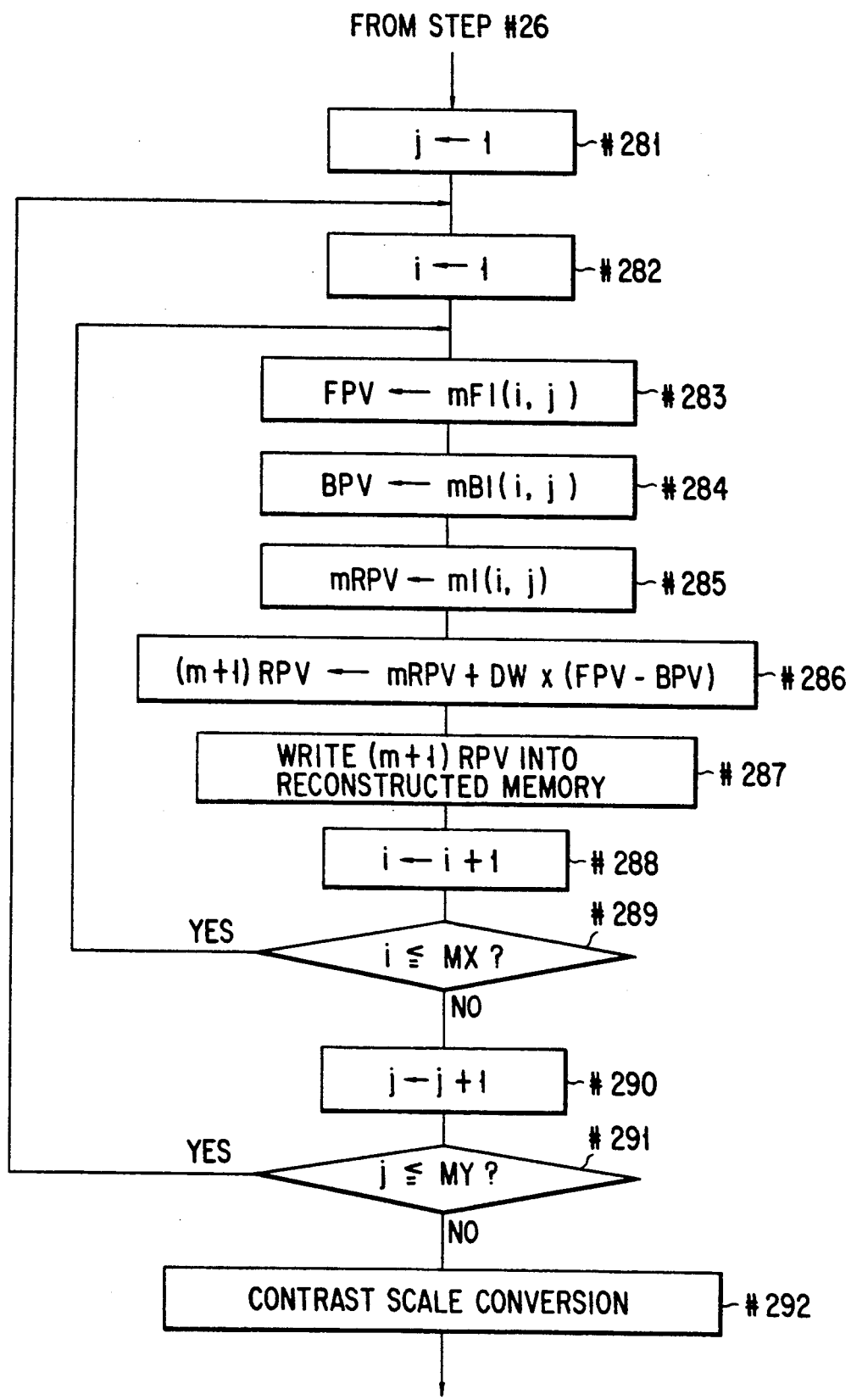
FIG. 10 is a detailed flow chart showing reconstruction processing of the (m+1)th image in the flow chart in FIG. 5.

FIG. 10 is a detailed flow chart of step #28 of FIG. 5 for reconstructing the (m+1)th image. Assumed that the matrix size of an image is set to be MX (pixels). MY (pixels). In step #281, j=1 is set. In step #282, i=1 is set. In step #283, a pixel value at an address (i,j) of the F-image memory 52 is read out as a value FPV. In step #284, a pixel value at the address (i,j) of the B-image memory 50 is read out as a value BPV. In step #285, a pixel value at the address (i,j) of the reconstructed image memory 54 is read out as a value mRPV.

In step #286, the following calculation is performed:

$$(m+1)RPV = mRPV + DW \times (FPV - BPV) \qquad (33)$$

where DW is the inclination (difference) of the primary interpolation coefficients for helical scanning.

In step #287, (m+1)RPV is written at the address (i,j) of the reconstructed image memory 54. In step #288, i=i+1 is set. In step #289, it is determined whether i is not larger than MX. If YES in step #289, the flow returns to step #283. If NO in step #289, j=j+1 is set in step #290. In step #291, it is determined whether j is not larger than MY. If YES in step #291, the flow returns to step #282. If NO in step #291, all the pixel values of the reconstructed image are converted into the CT values by the contrast scale circuit 62 in step #292. The CT image data is stored in the CT image memory 64.

The detailed flow chart of step #34 of FIG. 5 for reconstructing the (m−1)th image is the same as that shown in FIG. 10 except that the equation of step #286: $(m+1)RPV = mRPV + DW$ (FPV−BPV) is changed to a following equation:

$$(m-1)RPV = mRPV - DW (FPV - BPV) \qquad (34)$$

Figure 11:
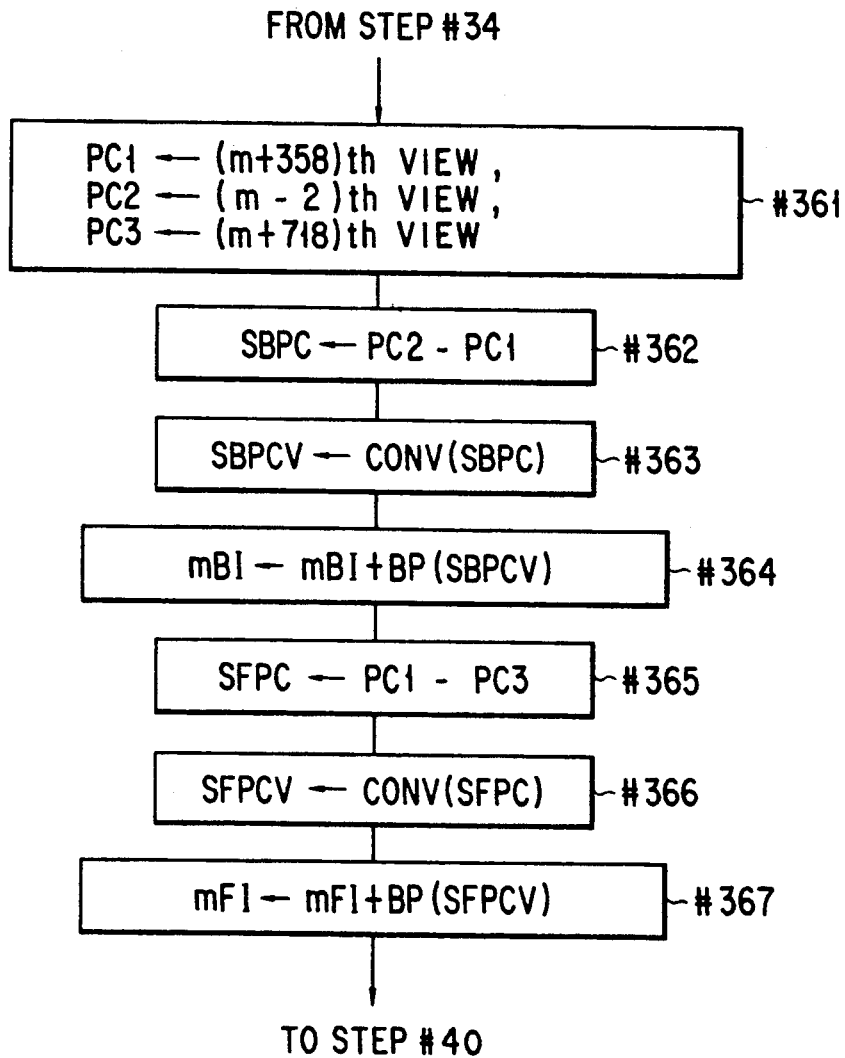
FIG. 11 is a detailed flow chart showing reconstruction processing of the (m−1)th B-image and the (m−1)th F-image in the flow chart in FIG. 5.

FIG. 11 is a detailed flow chart of steps #36 and #38 of FIG. 5 for reconstructing the (m−1)B-image and (m−1)F-image. First, the CPU 56 sends forth such instructions to the interpolation circuit 44, CONV circuit 46 and BP circuit 48 that indicate the reconstruction of the backward image, the inclination DW of the primary interpolation, the parameters necessary for the back projection (for the B-image and F-image), the convolution function and the like. Note that data which has already been stored in the reconstruction processing unit need not be transferred.

In step #361, the CPU 42 reads out three views, i.e., the (m+358)th view, the (m−2)th view and the (m+718)th view, from the raw data memory 40, and supplies them to the interpolation (difference) circuit 44. In this case, these views are respectively represented by PC1, PC2 and PC3.

In step #362, the interpolation (difference) circuit 44 performs a calculation of PC2−PC1, and transfers the calculation result, as a difference SBPC, to the CONV circuit 46. In step #363, the CONV circuit 46 performs convolution processing of the difference SBPC with the convolution function. Convolution processing can be performed by using a known technique. The convolution result is represented by SBPCV. In step #364, the BP circuit 48 performs back projection of the convolution result SPBCV by superposing (adding) the convolution result SBPCV on the B-image mBI in the B-image memory 50. Back projection processing can be performed by using a known technique. The parameters necessary for the back projection processing of the B-image are generated from the parameter setting device 58 under the control of the CPU 56 and are transferred to the BP circuit 48.

In step #365, the interpolation (difference) circuit 44 performs a calculation of PC1−PC3, and transfers the calculation result, as a difference SFPC, to the CONV circuit 46. In step #366, the CONV circuit 46 performs convolution processing of the difference SFPC with the convolution function. The convolution result is represented by SFPCV. In step #367, the BP circuit 48 performs back projection of the convolution result SPFCV by superposing (adding) the convolution result SFPCV on the F-image mFI in the F-image memory 52. The parameters necessary for the back projection processing of the F-image are generated from the parameter setting device 58 under the control of the CPU 56 and are transferred to the BP circuit 48.

Note that step #362 to step #364 and step #365 to step #367 may be partly or completely multiplexed to be executed by different circuits, different printed circuit boards, or different units.

As described above, according to this embodiment, a tomographic image at one slice position is obtained by normal reconstruction processing upon interpolation processing of views corresponding to two rotations, and a tomographic image at an adjacent slice position is obtained by reconstructing only the difference in view between the two slice positions, multiplying the reconstructed data by a coefficient, and adding the product to the tomographic image. With this operation, interpolation and reconstruction of 360° views need not be performed at each slice position. Therefore, images at consecutive slice positions in the helical scanning scheme can be obtained at high speed. If the adjacent slice position is continuously changed by using a mouse or the like, images at the respective slice positions can be continuously displayed, thus allowing continuous observation of the interior of a human body.

Other embodiments will be described hereinafter. The circuit configuration of the other embodiments is the same as that of the first embodiment so that the description thereof is omitted. Further, the some portions of the operation of the other embodiment are the same as that of the first embodiment so that the description thereof is also omitted.

Figure 12:
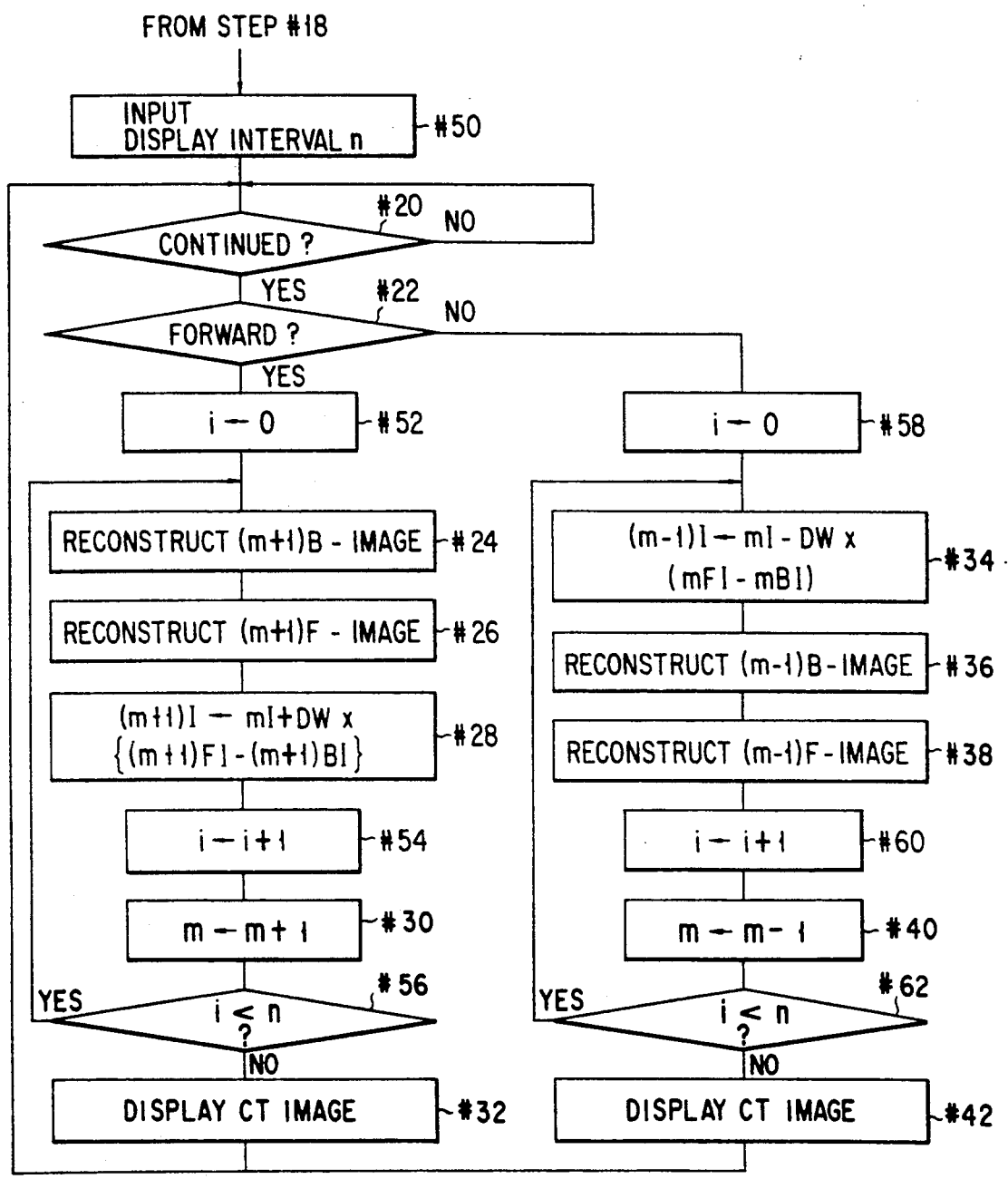
FIG. 12 is a flow chart showing the image reconstructing process of a second embodiment in which the CT image is displayed for every plural slices n.

In the first embodiment, adjacent images are sequentially reconstructed and displayed. However, a display operation may be performed at intervals of plurality of slice positions. A second embodiment employing such a display scheme will be described next. FIG. 12 is a flow chart of this scheme. Since step #10 to step #18 in which the mF-image is reconstructed are the same as those in the first embodiment, an illustration thereof will be omitted. In step #50, a display slice interval n (n≧1) is designated.

If the forward direction is designated in step #22, i=0 is set in step #52, and step #24, step #26 and step #28 are executed. In step #54, i=i+1 is set. In step #30, m=m+1 is set. In step #56, it is determined whether i is smaller than n. If YES in step #56, the flow returns to step #24. If NO in step #56, the CT image corresponding to the image (m+1)I obtained in step #28 is displayed in step #32.

If the backward direction is designated in step #22, i=0 is set in step #58, and step #34, step #36 and step #38 are executed. In step #60, i =i+i+1 is set. In step #40, m=m−1 i set. In step #62, it is determined whether i is smaller than n. If YES in step #62, the flow returns to step #34. If NO in step #62, the CT image corresponding to the image (m-1)I obtained in step #34 is displayed in step #42.

In the first and second embodiments, a tomographic image is obtained at each slice position regardless of whether or not display is performed. A third embodiment in which tomographic images are obtained at intervals of a plurality of slice positions will be described next. This scheme can be applied to the first and second embodiments. A case wherein the scheme is applied to the second embodiment will be described below with reference to the flow chart shown in FIG. 13. The step #10 25 to step #22 in which the slice changing direction is determined are the same as those in the second embodiment, an illustration thereof is omitted. If the forward direction is designated in step #22, the flow advances to step #64. If the backward direction is designated in step #22, the flow advances to step #83.

If the forward direction is designated, i =1 is set in step #64. In step #65, the (m+1)th B-image is reconstructed according to equation (15). In step #66, the (m+1)th F-image is reconstructed according to equation (16). In step #67, the (m+1)th B-image is stored in a memory SIGB. In step #68, the (m+1)th F-image is stored in a memory SIGF. In step #69, m=m+1 is set. In step #70, it is determined whether n equals to 1. The parameter n is set in step #50 of FIG. 12.

If YES in step #70, the flow advances to step #80. If NO in step #70, the (m+1)th B-image is reconstructed according to equation (15) in step #71. In step #72, the (m+1)th F-image is reconstructed according to equation (16). In step #73, data obtained by adding the (m+1)th B-image to the data in the memory SIGB is newly stored in the memory SIGB. In step #74, data obtained by adding the (m+1)th F-image to the data in the memory SIGF is newly stored in the memory SIGF. In step #76, m=m+1 is set. In step #77, i=i+1 is set. In step #78, it is determined whether i is smaller than n.

If YES in step #78, the flow returns to step #71. If NO in step #78, an m-th image mI to be displayed next is obtained in step #80 according to the following equation:

$$mI=(m-n)I+DW\times(SIGF-SIGB) \quad (35)$$

where (m-n)I is the currently displayed image.

In step #82, the CT image corresponding to the image mI obtained in step #80 is displayed, and the flow returns to step #20.

If the backward direction is designated in step #22, i =1 is set in step #83. In step #84, the m-th B-image is stored in the memory SIGB. In step #85, the m-th F-image is stored in the memory SIGF. In step #86, the (m−1)th B-image is reconstructed according to equation (19). In step #87, the (m−1)th F-image is reconstructed according to equation (20). In step #88, m=m−1 is set. In step #89, it is determined whether n equals to 1.

If YES in step #89, the flow advances to step #97. If NO in Step #89, data obtained by adding the m-th B-image to the data in the memory SIGB is newly stored in the memory SIGB in step #90. In step #91, data obtained by adding the m-th F-image to the data in the memory SIGF is newly stored in the memory SIGF. In step #92, the (m−1)th B-image is reconstructed according to equation (19). In step #93, the (m-1)th F-image is reconstructed according to equation (20). In step #94, m=m−1 is set. In step #95, i=i+1 is set. In step #96, it is determined whether i is smaller than n.

If YES in step #96, the flow returns to step #90. If NO in step #96, an m-th image mI to be displayed next is obtained in step #97 according to the following equation:

$$(m+n)I-DW\times(SIGF-SIGB) \quad (36)$$

where (m+n)I is the currently displayed image.

In step #98, the CT image corresponding to the image mI obtained in step #97 is displayed, and the flow returns to step #20.

Equation (35) will be proved next. If m=m+n−1 is set in equation (23), equation (35) can be obtained as follows:

$$\begin{aligned}(m+n)I &= (m+n-1)I + DW \times \{(m+n)FI - (m+n)BI\} \\ &= (m+n-2)I + \sum_{i=1}^{2} \{(m+n+1-i)FI - (m+n+1-i)BI\} \\ &= mI + \sum_{i=1}^{n} \{(m+n+1-i)FI - (m+n+1-i)BI\} \\ &= mI + \sum_{i=1}^{n} \{(m+i)FI - (m+i)BI\}\end{aligned}$$

Similarly, equation (36) can be obtained by setting m=m−n+1 in equation (25) and developing it in the same manner as described above.

In the above-described embodiments, the slice position is sequentially changed in the forward and backward directions by using the switches. However, a desired slice position may be designated by interlocking using a pointer such as a mouse or a track ball. In this case, instead of performing the processing in step #20 and step #22 in each embodiment, a signal from a pointer such as a mouse is read. If no change in signal occurs, the flow returns to step #20. If a change occurs, the number "n" of slices by which the slice position is to be changed is obtained by multiplying the amount of change by a predetermined coefficient. If n>0, processing associated with the forward direction is executed If n<0, processing associated with the backward direction is executed.

Figure 14:
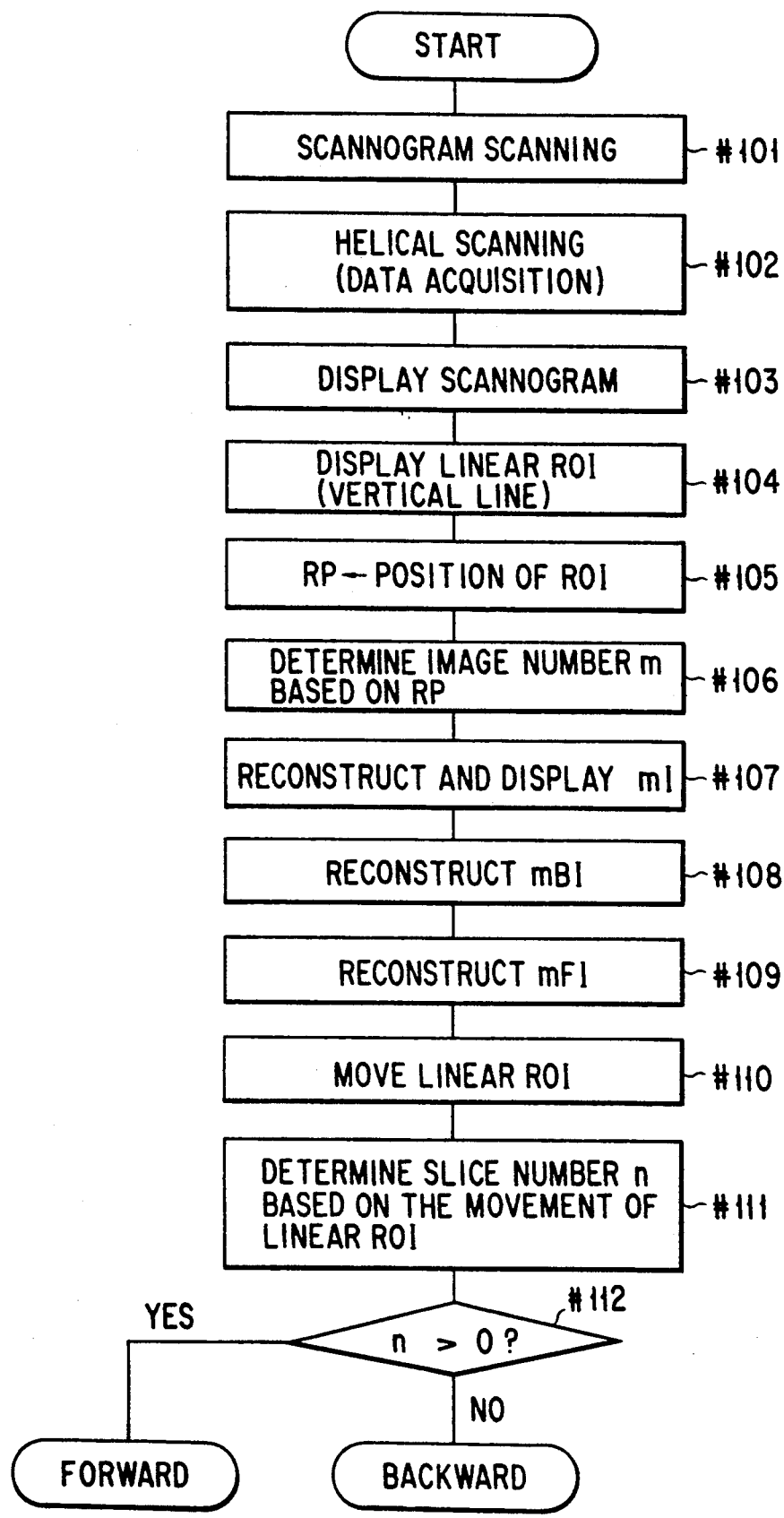
FIG. 14 is a flow chart showing the image reconstructing process of a fourth embodiment in which the CT image is reconstructed at a slice position which is designated by a line cursor in a scannogram.

In the above-described scheme, the slice position is changed by interlocking using a pointer such as a mouse or a track ball. A fourth embodiment obtained by further modifying this scheme will be described below. In general, the display device of an X-ray CT apparatus displays a scannogram (a projected image picked up by moving only the bed without rotating the X-ray tube) together with a vertical line ROI cursor superposed on the scannogram. The display position of the ROI cursor is moved by a mouse or the like. In the fourth embodiment, the slice position is matched with the position of the vertical line ROI on the scannogram. FIG. 14 is a flow chart showing an operation of the fourth embodiment.

In step #101, a scannogram is photographed. In step #102, helical scanning is performed to acquire views. In step #103, the scannogram is displayed on part of the L image display device. In step #104, a vertical ROI cursor is superposed and displayed on the scannogram. In step #105, a position RP of the vertical line ROI cursor is detected. In step #106, an image number m corresponding to the cursor position RP is obtained.

In step #107, the current image mI is reconstructed according to equation (12) and displayed. In step #108, the current mB-image is reconstructed according to equation (13). In step #109, the current mF-image is reconstructed according to equation (14). In step #110, the display position of the vertical line ROI cursor on the scanogram is moved by using a mouse or the like.

In step #111, the cursor position RP is changed, and the amount of change is detected, thereby obtaining the number "n" of changing slice by multiplying the amount of change by a predetermined coefficient. In step #112, it is determined whether n is larger than 0. If YES in step #112, step #24 or step #64 is executed, similar to the case wherein the forward direction is designated in step #22 in the above-described embodiments. If NO in step #112, step #34 or step #83 is executed, similar to the case wherein the backward direction is designated in step #22 in the above-described embodiments.

Note that a helical scan may be performed as a prescan for positioning, and the function of this embodiment may be used for a scan-planning on the scannogram.

In the above embodiment, no reconstructed images are stored. However, designated images may be stored in the image memory as needed.

In addition, images at designated slice positions may be reconstructed, displayed, and stored by another method, e.g., a method using reflection data, as needed.

Figure 15:
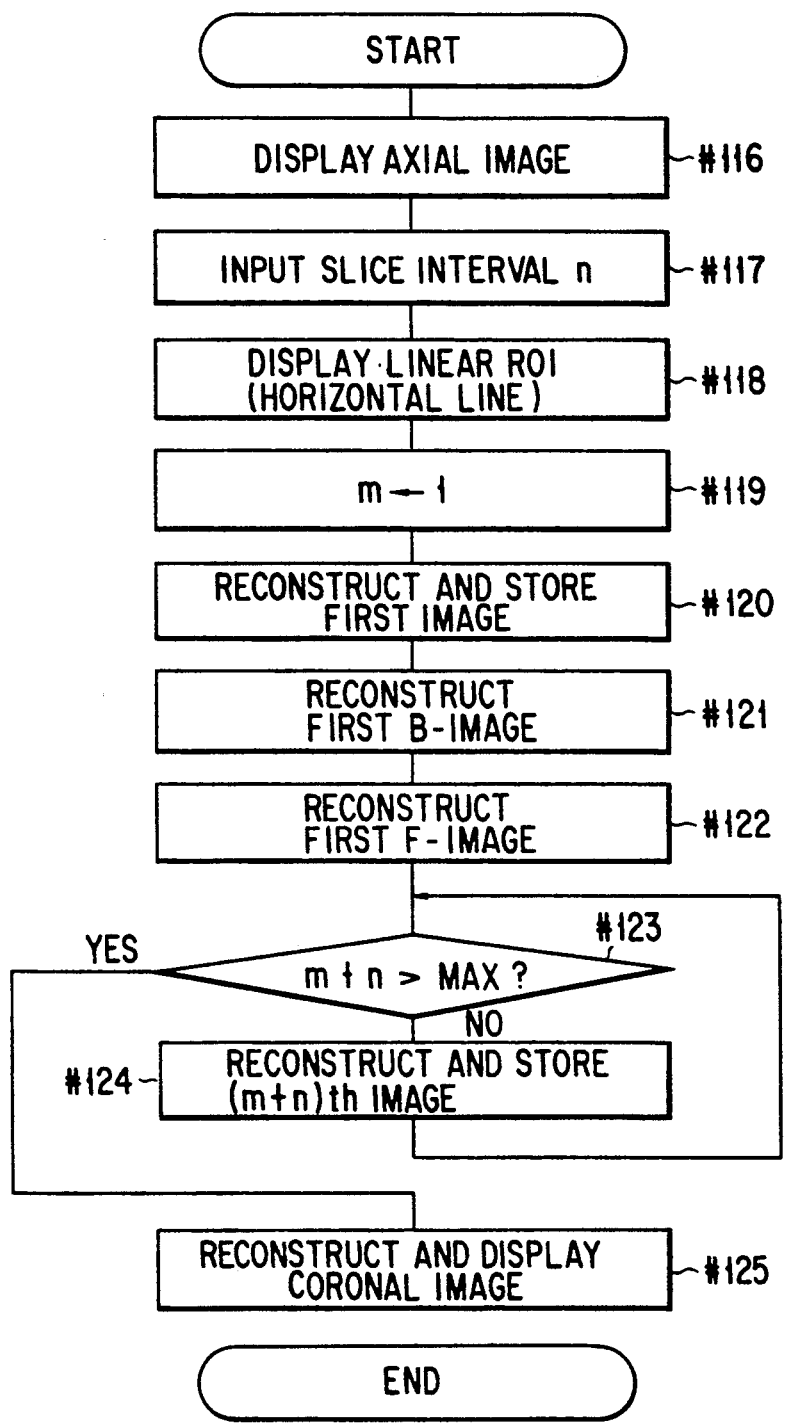
FIG. 15 is a flow chart showing the image reconstructing process of a fifth embodiment in which an MPR image is displayed.

A fifth embodiment of the present invention will be described next. In the fifth embodiment, one of a plurality of axial images is partly reconstructed, and coronal, sagittal and oblique images for a multi-planar reconstruction (MPR) display are formed from the reconstructed image to be displayed. In a conventional MPR display, since the interval of an axial image is large as compared with the size of an axial image pixel, stepped portions are displayed on the ordinate (or abscissa) of an MPR image. However, in this embodiment, since the interval of an axial image can be reduced, an MPR image having no stepped portions can be reconstructed. FIG. 15 is a flow chart showing an operation of the fifth embodiment, in which a coronal image is reconstructed. This embodiment can be equally applied to reconstruction of sagittal and oblique images.

In step #116, a proper axial image is displayed by the scheme of one of the above-described embodiments. In step #117, a slice interval "n" of an axial image to be reconstructed is designated to form a coronal image. In step #118, a horizontal line ROI cursor is displayed at a position on the displayed axial image at which a coronal image is to be reconstructed. In step #119, m=1 is set. Subsequently, back projection and image storage processing are executed with respect to only the pixels of one line on which the horizontal line ROI cursor is displayed.

In step #120, an image (first image) is reconstructed according to equation (12) and stored. In step #121, the first B-image is reconstructed according to equation (13). In step #122, the first F-image is reconstructed according to equation (14). In step #123, it is determined whether or not (m+n) is larger than the maximum slice number of images.

Figure 13:
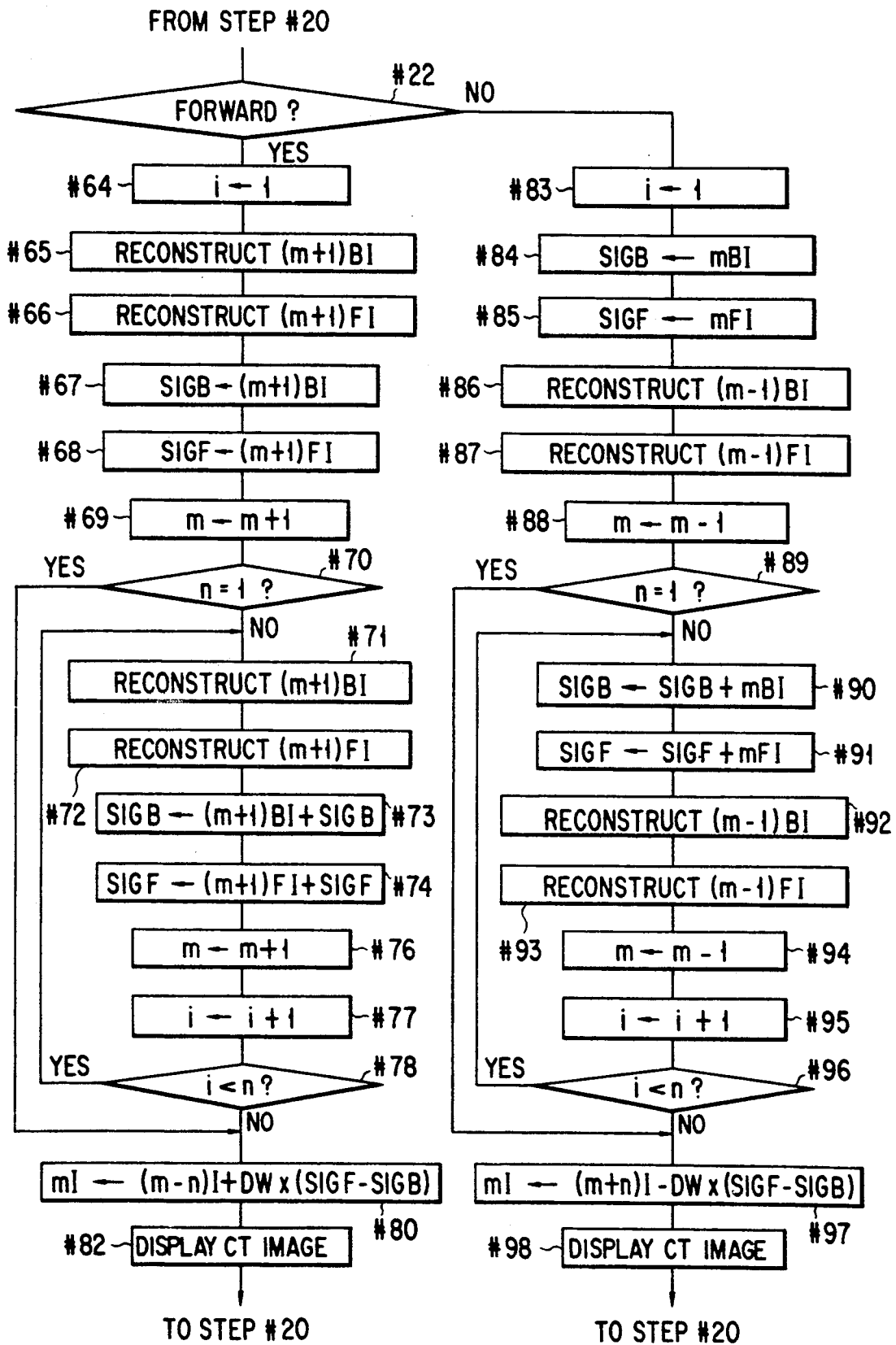
FIG. 13 is a flow chart showing the image reconstructing process of a third embodiment in which the CT image is reconstructed and displayed for every plural slices n.

If NO in step #123, the flow advances to step #124 to reconstruct and store the (m+n)th image by the processing in step #64 to step #80 in the third embodiment shown in FIG. 13. Thereafter, the flow returns to step #123. Similar to the above case, reconstruction is performed with respect to only the pixels of one line on which the horizontal line ROI cursor is displayed. In YES in step #123, a coronal image is reconstructed from the stored image by a known method and is displayed in step #125.

In the fifth embodiment, one MPR image is formed. However, an axial image (including a line ROI cursor) and an MPR image may be simultaneously displayed. In this case, the line ROI cursor is moved by a mouse, and the MPR image is reconstructed and displayed in correspondence with the position of the line ROI cursor. With this operation, MPR images can be continuously observed.

A sixth embodiment of the present invention will be described next. The sixth embodiment can be formed by modifying the fifth embodiment such that a plurality of axial images are reconstructed, and a three-dimensional image (surface display or the like) is formed from these images so as to be displayed. In a conventional threedimensional image display scheme, since the interval of an axial image is larger as compared with the size of an axial image pixel, stepped portions are displayed in the direction of slice thickness. According to this embodiment, since the interval of an axial image can be reduced, a three-dimensional image having no stepped portions can be reconstructed. Step #116 to step #124 of the fifth embodiment in which the (m-n)th image is reconstructed are similarly performed in this embodiment. However, the reconstruction in step #120, step #122 and step #124 in the fifth embodiment is performed with respect to all pixels in this embodiment. This embodiment ca be realized by forming a three-dimensional image from stored images, instead of reconstructing a coronal image in step #125 in the flow chart shown in FIG. 15, and displaying the threedimensional image.

In the above-described embodiments, a slice and a view image are located at the same position. However, by modifying the equations, the present invention can be applied to a case wherein a slice and a view are located at different positions.

Similarly, in a case wherein the interval of slice positions is not an integer multiple of the interval of view positions, the present invention can be executed by modifying the equations. Therefore, in the fifth embodiment and its modification, the interval of slice positions can be matched with the pitch of the pixels of an axial image.

As has been described above, according to the present invention, a tomographic image separated from the current image by n slices can be reconstructed by only performing convolution and back projection 2n times and addition/subtraction of images. Since the time required to execute addition/subtraction of images is short, the reconstruction time substantially corresponds to the time required to perform convolution and back projection 2n times. In contrast to this, the time normally required for reconstruction corresponds to the time required to perform convolution and back projection a number of times equal to the number of views within 360°. Since "2n" is generally much smaller than the number of views within 360°. a tomographic image separated from the current image by 2n slices can be reconstructed in a short period of time according to the present invention. Therefore, continuous images obtained by helical scanning can be observed in a substantially real-time manner. In addition, since only necessary images can be stored, a large image storage capacity is not required. Furthermore, an MPR image having few stepped portions can be reconstructed.

The present invention is not limited to the abovedescribed embodiment. Various changes and modifications can be made within the spirit and scope of the invention.

What is claimed is:

1. An X-ray computerized tomography apparatus for acquiring views by helical scanning, comprising:
    means for obtaining a tomographic image at a first slice position by reconstructing views which are obtained by interpolating 360° views in a first range next to the first slice position in a backward direction in which a slice position number decreases and 360° views in a second range next to the first slice position in a forward direction in which the slice position number increases;
    means for obtaining a first backward image by reconstructing the views in the first range without interpolation processing;
    means for obtaining a first forward image by reconstructing the views in the second range without interpolation processing;
    means for obtaining a second backward image by reconstructing a view obtained by subtracting a view at a position separated from the first slice position by 360° in the backward direction from a view at the first slice position, and adding the result of reconstruction to the first backward image;
    means for obtaining a second forward image by reconstructing a view obtained by subtracting a view at the first slice position from a view at a position separated from the first slice position by 360° in the forward direction, and adding the result of reconstruction to the first forward image; and
    means for obtaining a tomographic image at a second slice position which is separated from the first slice position by 360° in the forward direction by multiplying a difference between the second forward image and the second backward image by a coefficient, and adding the result of multiplication to the tomographic image at the first slice position.

2. An X-ray computerized tomography apparatus according to claim 1, further comprising:
    means for updating the first forward image by reconstructing a view obtained by subtracting a view at a position separated from the first slice position by one view angle in the forward direction from a view at a position separated from the first slice position by 360° plus one view angle in the forward direction.

3. An X-ray computerized tomography apparatus for acquiring views by helical scanning, comprising:
    means for obtaining a tomographic image at a first slice position by reconstructing views at the first slice position which are obtained by interpolating 360° views in a first range next to the first slice position in a backward direction in which a slice position number decreases and 360° views in a second range next to the first slice position in a forward direction in which the slice position number increases;
    means for obtaining a first backward image by reconstructing the views in the first range without interpolation processing;
    means for obtaining a first forward image by reconstructing the views in the second range without interpolation processing; and
    means for obtaining a tomographic image at a second slice position which is separated from the first slice position by 360° in the backward direction by multiplying a difference between the first forward image and the first backward image by a coefficient, and subtracting the result of multiplication from the tomographic image at the first slice position.

4. An X-ray computerized tomography apparatus according to claim 3, further comprising:
    means for updating the first backward image by reconstructing a view obtained by subtracting a view at a position separated from the first slice position by one view angle in the backward direction from a view at a position separated from the first slice position by 360° plus one view angle in the backward direction.

5. An X-ray computerized tomography apparatus for acquiring views by helical scanning, comprising:
    first memory means for obtaining a tomographic image at a first slice position by reconstructing views at the first slice position which are obtained by interpolating 360° views in a first range next to the first slice position in a backward direction in which a slice position number decreases and 360° views in a second range next to the first slice position in a forward direction in which the slice position number increases;
    second memory means for obtaining a first backward image by reconstructing the views in the first range without interpolation processing;
    third memory means for obtaining a first forward image by reconstructing the views in the second range without interpolation processing;
    means for obtaining a second backward image by reconstructing a view obtained by subtracting a view at a position separated from the first slice position by 360° in a backward direction from a view at the first slice position, and adding the result of reconstruction to the first backward image;
    mean for obtaining a second forward image by reconstructing a view obtained by subtracting a view at the first slice position from a view at a position separated from the first slice position by 360° in the forward direction, and adding the result of reconstruction to the first forward image;

writing means for obtaining a tomographic image at a second slice position which is separated from the first slice position by 360° in the forward direction by multiplying a difference between the second forward image and the second backward image by a coefficient, and adding the result of multiplication to the tomographic image obtained at the first slice position and for writing the tomographic image obtained at the second slice position into said first memory means; and fourth m emory means for storing tomographic images obtained by performing contrast scale conversion of the tomographic images obtained at the first and second slice positions and stored in said first memory means.

6. An X-ray computerized tomography apparatus according to claim 5, in which said writing means writes tomographic images obtained at all slice positions into said first memory means, and all the tomographic images stored in said fourth memory means are displayed.

7. An X-ray computerized tomography apparatus according to claim 5, in which said writing means writes tomographic images obtained at slices with a predetermined interval, and all the tomographic images stored in said fourth memory means are displayed.

8. An X-ray computerized tomography apparatus according to claim 5, further comprising:
mean for picking-up and displaying a scannogram; and
means for displaying a linear cursor on the scannogram which designates the first slice position and the second slice position.

9. An X-ray computerized tomography apparatus according to claim 5, in which said fourth memory means comprises:
means for storing plural tomographic images;
means for designating a desired slice position; and
means for botanizing a coronal, sagittal or oblique image based on the tomographic image at the position designated by said designating means.

10. An X-ray computerized tomography apparatus for acquiring views by helical scanning, comprising:
first memory means for obtaining a tomographic image at a first slice position by reconstructing views at the first slice position which are obtained by interpolating 360° views in a first range next to the first slice position in a backward direction in which a slice position number decreases and 360° views in a second range next to the first slice position in a forward direction in which the slice position number increases;

second memory means for obtaining a backward image by reconstructing the views in the second range without interpolation processing;

third memory means for obtaining a forward image by reconstructing the views in the first range without interpolating processing;

writing means for obtaining a tomographic image at a second slice position which is separated from the first slice position by 360° in the backward direction by multiplying a difference between the forward image and the backward image by a coefficient, and subtracting the result of multiplication from th e tomographic image obtained at the first slice position and for writing the tomographic image obtained at the second slice position into said first memory means; and fourth memory means for storing tomographic images obtained by performing contrast scale conversion of the tomographic images obtained at the first and second slice positions and stored in said first memory means.

11. An X-ray computerized tomography apparatus according to claim 10, further comprising:
means for updating the backward image stored in said second memory means by reconstructing a view obtained by subtracting a view at a position separated from the first slice position by one view angle in the backward direction from a view at a position separated from the first slice position by 360° plus one view angle in the backward direction, and adding the result of reconstruction to the backward image stored in said second memory means.

12. An X-ray computerized tomography apparatus according to claim 10, in which said writing means writes tomographic images obtained at all slice positions into said first memory means, and all the tomographic images stored in said fourth memory means are displayed.

13. An X-ray computerized tomography apparatus according to claim 10, in which said writing means writes tomographic images obtained at slices with a predetermined interval, and all the tomographic images stored in said fourth memory means are displayed.

14. An X-ray computerized tomography apparatus according to claim 10, further comprising:
means for picking-up and displaying a scannogram; and
means for displaying a linear cursor on the scannogram which designates the first slice position and the second slice position.

15. An X-ray computerized tomography apparatus according to claim 10, in which said fourth memory means comprises:
means for storing plural tomographic images;
means for designating a desired slice position; and
means for obtaining a coronal, sagittal or oblique image based on the tomographic image at the position designated by said designating means.

* * * * *

UNITED STATES PATENT AND TRADEMARK OFFICE
CERTIFICATE OF CORRECTION

PATENT NO. : 5,315,665
DATED : May 24, 1994
INVENTOR(S) : Akinami OHHASHI

It is certified that error appears in the above-indentified patent and that said Letters Patent is hereby corrected as shown below:

On the title page, item [54] and column 1, line 7, change "360" to to --360°--.

Title page, third from last line of the Abstract, after "X" insert --{--.

Claim 5, column 20, line 65, change "mean" to --means--.

Claim 5, column 21, line 13, change "m emory" to --memory--.

Claim 9, column 21, line 44, change "botanizing" to --obtaining--.

Claim 10, column 22, line 6, change "interpolating" to --interpolation--.

UNITED STATES PATENT AND TRADEMARK OFFICE
CERTIFICATE OF CORRECTION

PATENT NO. : 5,315,665
DATED : May 24, 1994
INVENTOR(S) : Akinami OHHASHI

It is certified that error appears in the above-indentified patent and that said Letters Patent is hereby corrected as shown below:

Claim 10, column 22, line 13, change "th e" to --the--.

Signed and Sealed this

Twenty-first Day of March, 1995

Attest:

BRUCE LEHMAN

Attesting Officer     Commissioner of Patents and Trademarks